(12) United States Patent
Jaeger et al.

(10) Patent No.: US 10,036,020 B2
(45) Date of Patent: Jul. 31, 2018

(54) COMPOSITIONS AND METHODS FOR INHIBITING JC VIRUS (JCV)

(71) Applicant: The United States of America, as represented by the Secretary, Department of Health & Human Services, Washington, DC (US)

(72) Inventors: Laura B. Jaeger, North Bethesda, MD (US); Avindra Nath, Ellicott City, MD (US); Eugene Major, Darnestown, MD (US); Maria Chiara Kushner-Monaco, Kensington, MD (US); Michael W. Ferenczy, Washington, DC (US)

(73) Assignee: The United States of America, as represented by the Secretary, Department of Health & Human Services, Washington, DC (US)

( * ) Notice: Subject to any disclaimer, the term of this patent is extended or adjusted under 35 U.S.C. 154(b) by 0 days.

(21) Appl. No.: 15/023,352

(22) PCT Filed: Sep. 19, 2014

(86) PCT No.: PCT/US2014/056655
§ 371 (c)(1),
(2) Date: Mar. 18, 2016

(87) PCT Pub. No.: WO2015/042466
PCT Pub. Date: Mar. 26, 2015

(65) Prior Publication Data
US 2016/0272974 A1    Sep. 22, 2016

Related U.S. Application Data

(60) Provisional application No. 61/879,833, filed on Sep. 19, 2013.

(51) Int. Cl.
| | | |
|---|---|---|
| A61K 31/7115 | (2006.01) | |
| A61K 31/712 | (2006.01) | |
| A61K 31/7125 | (2006.01) | |
| C12N 15/113 | (2010.01) | |
| C07K 16/08 | (2006.01) | |

(52) U.S. Cl.
CPC ........ *C12N 15/1131* (2013.01); *C07K 16/084* (2013.01); *C12N 2310/11* (2013.01); *C12N 2310/315* (2013.01); *C12N 2310/346* (2013.01); *C12N 2710/22011* (2013.01)

(58) Field of Classification Search
None
See application file for complete search history.

(56) References Cited

U.S. PATENT DOCUMENTS

| | | |
|---|---|---|
| 4,426,330 A | 1/1984 | Sears |
| 4,534,899 A | 8/1985 | Sears |
| 4,707,448 A | 11/1987 | Major |
| 5,013,556 A | 5/1991 | Woodle et al. |
| 5,108,921 A | 4/1992 | Low et al. |
| 5,213,804 A | 5/1993 | Martin et al. |
| 5,227,170 A | 6/1993 | Sullivan |
| 5,264,221 A | 11/1993 | Tagawa et al. |
| 5,354,844 A | 10/1994 | Beug et al. |
| 5,356,633 A | 10/1994 | Woodle et al. |
| 5,395,619 A | 3/1995 | Zalipsky et al. |
| 5,416,016 A | 5/1995 | Low et al. |
| 5,417,978 A | 5/1995 | Tari et al. |
| 5,459,127 A | 10/1995 | Felgner et al. |
| 5,462,854 A | 10/1995 | Coassin et al. |
| 5,469,854 A | 11/1995 | Unger et al. |
| 5,512,295 A | 4/1996 | Kornberg et al. |
| 5,521,291 A | 5/1996 | Curiel et al. |
| 5,527,528 A | 6/1996 | Allen et al. |
| 5,534,259 A | 7/1996 | Zalipsky et al. |
| 5,543,152 A | 8/1996 | Webb et al. |
| 5,543,158 A | 8/1996 | Gref et al. |
| 5,547,932 A | 8/1996 | Curiel et al. |
| 5,556,948 A | 9/1996 | Tagawa et al. |
| 5,580,575 A | 12/1996 | Unger et al. |
| 5,583,020 A | 12/1996 | Sullivan |
| 5,591,721 A | 1/1997 | Agrawal et al. |
| 5,595,756 A | 1/1997 | Bally et al. |
| 6,287,860 B1 | 9/2001 | Monia et al. |
| 6,656,730 B1 | 12/2003 | Manoharan et al. |
| 6,887,906 B1 | 5/2005 | Teng |

(Continued)

FOREIGN PATENT DOCUMENTS

| | | |
|---|---|---|
| WO | WO 1993/007883 | 4/1993 |
| WO | WO 1994/026764 | 11/1994 |

(Continued)

OTHER PUBLICATIONS

Radhakrishnan et al (J. Virol. 78(13): 7264-7269, 2004).*
Wolfrum et al (Nature Biotechnology 25(10): 1149-1157, 2007).*
Tomoko Matoba et al: "An siRNA against JC virus (JCV) agnoprotein inhibits JCV infection in JCV-producing cells inoculated in nude mice", Neuropathology, vol. 28, No. 3, Jun. 1, 2008 (Jun. 1, 2008), pp. 286-294.
G. J. Seo et al: "Evolutionarily Conserved Function of a Viral MicroRNA", Journal of Virology, vol. 82, No. 20, Aug. 6, 2008 (Aug. 6, 2008), pp. 9823-9828.
Bruce J. Brew et al: "Progressive multifocal leukoencephalopathy and other forms of JC virus disease", Nature Reviews Neurology, vol. 6, No. 12, Dec. 1, 2010 (Dec. 12, 2010), pp. 667-679.
U.S. Appl. No. 09/315,298 Abandoned, May 20, 1999, Ching Leo Teng.
Altschul, et al., "Basic local alignment search tool", J Mol Biol. Oct. 5;215(3):403-410 (1990).
Bollag, et al., "JC virus small T antigen binds phosphatase PP2A and Rb family proteins and is required for efficient viral DNA replication activity", PLoS One 5:e10606 (2010).
Cinque, et al., "Progressive multifocal leukoencephalopathy complicating HIV-1 infection", Lancet Infect. Dis. 9:625-636 (2009).

(Continued)

*Primary Examiner* — Richard A Schnizer
(74) *Attorney, Agent, or Firm* — Bryan D. Zerhusen; Locke Lord LLP

(57) ABSTRACT

The instant invention provides compositions and methods for inhibiting the JC Virus (JCV), and that can be used, for example, for treating progressive multifocal leukoencephalopathy (PML). Antisense oligonucleotides are provided which are effective in inhibiting JCV replication or multiplication, alone or in a combination. In preferred embodiments, the oligonucleotides contain modifications.

19 Claims, 20 Drawing Sheets

(56) References Cited

U.S. PATENT DOCUMENTS

| | | | |
|---|---|---|---|
| 2003/0027780 A1 | 2/2003 | Hardee et al. | |
| 2003/0219770 A1* | 11/2003 | Eshleman | C12Q 1/6869 435/6.14 |
| 2004/0259767 A1 | 12/2004 | Nagashima et al. | |
| 2005/0287570 A1* | 12/2005 | Mounts | G01N 33/6803 435/6.16 |
| 2007/0249552 A1* | 10/2007 | Khalili | C12N 15/1131 514/44 A |
| 2009/0246754 A1* | 10/2009 | Kiefer | C12Q 1/701 435/5 |
| 2010/0227915 A1 | 9/2010 | Tan et al. | |
| 2015/0099791 A1* | 4/2015 | Krieg | C12N 15/113 514/44 A |

FOREIGN PATENT DOCUMENTS

| | | |
|---|---|---|
| WO | WO-2005112636 A2 | 12/2005 |
| WO | WO-2012143427 A1 | 10/2012 |

OTHER PUBLICATIONS

Clifford, et al., "A study of mefloquine treatment for progressive multifocal leukoencephalopathy: results and exploration of predictors of PML outcomes", J Neurovirol. Aug. 2013;19(4):351-358 (2013).

Crooke, et al.. "Antisense Research and Application", (Crooke, S.T., editor) Springer-Verlag Berlin Heidelberg, 1998, pp. 276-278.

De Mesmaeker, et al., "Antisense oligonucleotides", Acc. Chem. Res., 28, 366-374 (1995).

Dias, et al., "Antisense oligonucleotides: basic concepts and mechanisms", Mol. Cancer Ther. 1:347-355 (2002).

Dugan, et al., "Direct correlation between sialic acid binding and infection of cells by two human polyomaviruses (JC virus and BK virus)", J. Virol. 82:2560-2564 (2008).

Egli, et al., "Prevalence of polyomavirus BK and JC infection and replication in 400 healthy blood donors", J. Infect. Dis. 199:837-846 (2009).

Elbashir, et al., "Duplexes of 21-nucleotide RNAs mediate RNA interference in cultured mammalian cells", Nature, 2001, 411, 494-498.

Elbashir, et al., "RNA interference is mediated by 21- and 22-nucleotide RNAs", Genes Dev., 15, 188-200 (2001).

Elphick, et al., "The human polyomavirus, JCV, uses serotonin receptors to infect cells", Science 306:1380-1383 (2004).

Ferenczy, et al., "Clonal immortalized human glial cell lines support varying levels of JC virus infection due to differences in cellular gene expression", J Neuroimmune Pharmacol. Dec. 2013;8(5):1303-1319.

Ferenczy, et al., "Molecular biology, epidemiology, and pathogenesis of progressive multifocal leukoencephalopathy, the JC virus-induced demyelinating disease of the human brain", Clin. Microbiol. Rev. 25:471-506 (2012).

Fire, et al, "Potent and specific genetic interference by double-stranded RNA in Caenorhabditis elegans", Nature, 391, 806-811 (1998).

Frisque, et al., "Human polyomavirus JC virus genome", J Virol. Aug. 1984;51(2):458-469 (1984).

Frisque, R.J., "Regulatory sequences and virus-cell interactions of JC virus", Prog. Clin. Biol. Res. 105:41-59 (1983).

Houff, et al., "A rapid method for in situ hybridization for viral DNA in brain biopsies from patients with AIDS", AIDS 3:843-845 (1989).

Jensen, et al., "Viral variant nucleotide sequences help expose leukocytic positioning in the JC virus pathway to the CNS", J. Leukoc. Biol. 65:428-438 (1999).

Johnson, E.M. "Structural evaluation of new human polyomaviruses provides clues to pathobiology", Trends Microbiol. 18:215-223 (2010).

Johnson, et al., "Association of human Pur alpha with the retinoblastoma protein, Rb, regulates binding to the single-stranded DNA Pur alpha recognition element", J. Biol. Chem. 270:24352-24360 (1995).

Jones, et al., "Mefloquine distribution in postmortem cases", Forensic. Sci. Int. 68:29-32 (1994).

Kean, et al., "Seroepidemiology of human polyomaviruses", PLoS Pathog. 5:e1000363 1-10 (2009).

Lynch, et al., "DNA replication of chimeric JC virus-simian virus 40 genomes", Virology 204:819-822 (1994).

Lynch, et al., "Identification of critical elements within the JC virus DNA replication origin", J. Virol. 64:5812-5822 (1990).

Ma, et al., "Human CMV transcripts: an overview", Future Microbiol. May;7(5):577-593 (2012).

Major, E.O., "Progressive multifocal leukoencephalopathy in patients on immunomodulatory therapies", Annu Rev Med.;61:35-47 (2010).

Major, et al., "Establishment of a line of human fetal glial cells that supports JC virus multiplication", Proc. Natl. Acad. Sci. U. S. A. 82:1257-1261 (1985).

Marshall, et al., "Molecular regulation of JC virus tropism: insights into potential therapeutic targets for progressive multifocal leukoencephalopathy", J. Neuroimmune Pharmacol. 5:404-417 (2010).

Martin, et al., "A new access to 2'-O-Alkylated Ribonucleosides and Properties of 2'-O-Oligonucleotides", Helv. Chim. Acta, 78,486-504 (1995) (English Abstract only).

Mateen, et al., "Progressive multifocal leukoencephalopathy in transplant recipients", Ann. Neurol. 70:305-322 (2011).

Merabova, et al., "JC virus agnoprotein inhibits in vitro differentiation of oligodendrocytes and promotes apoptosis", J. Virol. 82:1558-1569 (2008).

Messam, et al., "Lineage pathway of human brain progenitor cells identified by JC virus susceptibility", Ann. Neurol. 53:636-646 (2003).

Montgomergy, et al., "RNA as a target of double-stranded RNA-mediated genetic interference in Caenorhabditis elegans", Proc. Natl. Acad. Sci., USA, 95, 15502-15507 (1998).

Neu, et al., "Structure-function analysis of the human JC polyomavirus establishes the LSTc pentasaccharide as a functional receptor motif", Cell Host Microbe 8:309-319 (2010).

Nukuzuma, et al., "Inhibitory effect of serotonin antagonists on JC Virus propagation in a carrier culture of human neuroblastoma cells", Microbiol. Immunol. 53:496-501 (2009).

O'Hara, et al., "Interferon beta1-a and selective anti- $5HT_{2a}$ receptor antagonists inhibit infection of human glial cells by JC virus", Virus Res. 132:97-103 (2008).

Okada, et al., "Distribution and function of JCV agnoprotein", J. Neurovirol. 7:302-306 (2001).

Orba, et al., "Inhibition of virus production in JC virus-infected cells by postinfection RNA interference", J. Virol. 78:7270-7273 (2004).

Ou, et al., "Analysis of minimal sequences on JC virus VP1 required for capsid assembly", J. Neurovirol. 7:298-301 (2001).

Pham, et al., "Cerebral uptake of mefloquine enantiomers in fatal cerebral malaria", Int. J. Clin. Pharmacol. Ther. 37:58-61 (1999).

Portnoy, et al., "Small RNA and transcriptional upregulation", Wiley Interdiscip. Rev. RNA 2:748-760 (2011).

Pruitt, A.A. "CNS infections in patients with cancer", Continuum (Minneap Minn) 18:384-405 (2012).

Radhakrishnan, et al., "Intracellular approach for blocking JC virus gene expression by using RNA interference during viral infection", J. Virol. 78:7264-7269 (2004).

Radulescu, R.T. "The 'LXCXE' hydropathic superfamily of ligands for retinoblastoma protein: a proposal", Med. Hypotheses. 44:28-31 (1995).

Rakoczy, P.E. "Antisense DNA technology", Methods Mol. Med. 47:89-104 (2001).

Sadiq, et al., "JCV detection in multiple sclerosis patients treated with natalizumab", J. Neurol. 257:954-958 (2010).

Saribas, et al., "JC virus agnoprotein enhances large T antigen binding to the origin of viral DNA replication: evidence for its involvement in viral DNA replication", Virology 433:12-26 (2012).

(56) References Cited

OTHER PUBLICATIONS

Schaumburg, et al., "Human embryonic stem cell-derived oligodendrocyte progenitor cells express the serotonin receptor and are susceptible to JC virus infection", J. Virol. 82:8896-8899 (2008).

Shishido-Hara, et al., "Major and minor capsid proteins of human polyomavirus JC cooperatively accumulate to nuclear domain 10 for assembly into virions", J. Virol. 78:9890-9903(2004).

Suzuki, et al., "Role of JC virus agnoprotein in virion formation", Microbiol. Immunol. 56:639-646 (2012).

Suzuki, et al., "The human polyoma JC virus agnoprotein acts as a viroporin", PLoS Pathog. 6:e1000801 (2010).

Tabara, et al.,"Reverse Genetics: RNAi in C. elegans: soaking in the genome sequence", Science, 282, 430-431 (1998).

Tan, et al., "PML-IRIS in patients with HIV infection: clinical manifestations and treatment with steroids", Neurology 72:1458-1464 (2009).

Tijsterman, et al., "RNA helicase MUT-14-dependent gene silencing triggered in C. elegans by short antisense RNAs", Science, 295, 694-697 (2002).

Timmons, et al., "Ingestion of bacterially expressed dsRNAs can produce specific and potent genetic interference in Caenorhabditis elegans", Gene, 263, 103-112 (2001).

Timmons, et al., "Specific interference by ingested dsRNA", Nature 395, 854 (1998).

Toovey, S., "Mefloquine neurotoxicity: a literature review", Travel Med. Infect. Dis.7:2-6 (2009).

Tuschl, et al., "Targeted mRNA degradation by double-stranded RNA in vitro", Genes Dev., 13, 3191-3197 (1999).

Wang, et al., "Inhibition of simian virus 40 large tumor antigen expression in human fetal glial cells by an antisense oligodeoxynucleotide delivered by the JC virus-like particle", Hum. Gene Ther. 15:1077-1090 (2004).

Weinberg, R.A., "E2F and cell proliferation: a world turned upside down", Cell 85:457-459 (1996).

Weinberg, R.A., "The retinoblastoma protein and cell cycle control", Cell 81:323-330 (1995).

White, et al., "Multiple roles for Puralpha in cellular and viral regulation", Cell Cycle 8:1-7 (2009).

Whitehead, et al., "Silencing or stimulation? siRNA delivery and the immune system", Annu. Rev. Chem. Biomol. Eng.2:77-96 (2011).

Zhang, et al., "PowerBLAST: a new network BLAST application for interactive or automated sequence analysis and annotation", Genome Res. Jun. 1997;7(6):649-656 (1997).

\* cited by examiner

FIG. 1B

| Name of antisense | Target to regions of JCV proteins in amino acids (aas) order | Corresponding to JCV genome | Size (nt) |
|---|---|---|---|
| LgT-1 | aas 8-15 of T-Ag, t-Ag | 4989-4970 | 20 |
| LgT-2 | aas 40-47 of T-Ag, t-Ag | 4897-4878 | 20 |
| JCV#3 | aas 97-104 of T-Ag | 4377-4357 | 20 |
| JCV#14 | aas 98-105 of T-Ag | 4375-4354 | 21 |
| JCV#8 | aas 58-65 of VP3 | 1058-1078 | 20 |
| JCV#13 | aas 57-64 of VP3 | 1055-1075 | 20 |
| VP1-2 | aas 12-17 from C-terminal of VP1 | 1506-1520 | 15 |
| VP1-3 | aas 33-40 from C-terminal of VP1 | 1570-1589 | 21 |
| VP1-4 | aas 337-344 from C-terminal of VP1 or aas 10-17 from N-terminal of VP1 | 2482-2502 | 21 |
| Scramble 1 | N/A | N/A | 21 |
| Scramble 3 | N/A | N/A | 22 |

FIG. 2A

Antisense DNAs

JCV#1: 5'-G*T*T*C*T*C*C*A*C*A*A*T*C*T*C*C*C*A*G*G*C-3'
JCV#2: 5'-T*C*T*C*C*A*C*A*A*T*C*T*C*C*C*A*G*G*C*T-3'
JCV#4: 5'-T*C*T*C*C*A*C*A*A*T*C*T*C*C*C*A*G*G*C*T*T-3'
JCV#5: 5'-T*T*C*T*C*C*A*C*A*A*T*C*T*C*C*C*A*G*G*C*T-3'
JCV#8: 5'-C*T*C*C*A*C*A*A*T*C*T*C*C*C*A*G*G*C*T*T-3'
JCV#9: 5'-T*T*C*T*C*C*A*C*A*A*T*C*T*C*C*C*A*G*G*C-3'
JCV#10: 5'-C*T*C*C*A*C*A*A*T*C*T*C*C*C*A*G*G*C*T*T*T-3'
JCV#11: 5'-C*T*C*C*A*C*A*A*T*C*T*C*C*C*A*G*G*C*T-3'
JCV#12: 5'-T*C*T*C*C*A*C*A*A*T*C*T*C*C*C*A*G*G*C-3'
JCV#13: 5'-G*T*T*C*T*C*C*A*C*A*A*T*C*T*C*C*C*A*G*G-3'

| JCV #3 | 4357-4377 | 20 |
| JCV #6 | 4357-4378 | 21 |
| JCV #7 | 4357-4376 | 19 |
| JCV #14 | 4354-4375 | 21 |
| JCV #15 | 4356-4376 | 20 |

| JCV #1 | 1055-1076 | 21 |
| JCV #2 | 1057-1077 | 20 |
| JCV #4 | 1057-1078 | 21 |
| JCV #5 | 1056-1077 | 21 |
| JCV #8 | 1058-1078 | 20 |
| JCV #9 | 1056-1076 | 20 |
| JCV #10 | 1058-1079 | 21 |
| JCV #11 | 1058-1077 | 19 |
| JCV #12 | 1057-1076 | 19 |
| JCV #13 | 1055-1075 | 20 |

| VP1-1 | 1461-1441 | 21 |
| VP1-2 | 1520-1506 | 15 |
| VP1-3 | 1589-1570 | 21 |
| VP1-4 | 2502-2482 | 21 |

| LgT-1 | 4989-4970 | 20 |
| LgT-2 | 4897-4878 | 20 |

Lg T-1: 5'-G*A*A*T*C*C*A*T*G*G*A*G*C*T*T*A*T*G*G*A-3'
Lg T-2: 5'-A*G*A*A*C*T*C*C*C*A*C*C*C*T*G*A*T*A*A*A*G-3'

JCV#3: 5'-G*T*C*T*T*C*A*T*C*C*C*A*C*T*T*C*T*C*A*T-3'
JCV#6: 5'-G*T*C*T*T*C*A*T*C*C*C*A*C*T*T*C*T*C*A*T*T-3'
JCV#7: 5'-G*T*C*T*T*C*A*T*C*C*C*A*C*T*T*C*T*C*A-3'
JCV#14: 5'-C*A*G*G*T*C*T*T*C*A*T*C*C*C*A*C*T*T*C*T*C
JCV#15: 5'-G*G*T*C*T*T*C*A*T*C*C*C*A*C*T*T*C*T*C*A-3'

Vp1-1: 5'-T*G*C*T*T*C*A*A*G*A*G*C*A*G*G*T*G*T*T*A*C-3'
Vp1-2: 5'-T*T*G*G*A*A*C*T*T*G*C*A*C*G*G*-3'
Vp1-3: 5'-T*T*C*T*A*C*C*T*C*T*G*T*A*A*T*T*G*A*G*T*C-3'
Vp1-4: 5'-T*T*G*T*C*A*A*C*G*T*A*T*C*T*C*A*T*C*A*T*G-3'

Scram 1: 5'-G*A*T*C*T*G*A*G*T*T*C*A*G*A*G*T*T*C*C*A*G-3'
Scram 3: 5'-C*A*G*T*G*T*G*T*G*T*C*T*G*A*G*A*A*G*C*T*C*A-3'
hCMV: 5' mG*C*G*T*T*T*G*C*T*C*T*T*C*T*T*G*C*mG-3'

Anti-T-Ag Antibody

Solvent control (-) pM1TC
(-) JCV#3

4.5ug pM1TC
(-) JCV#3

4ug pM1TC
5ug JCV#3

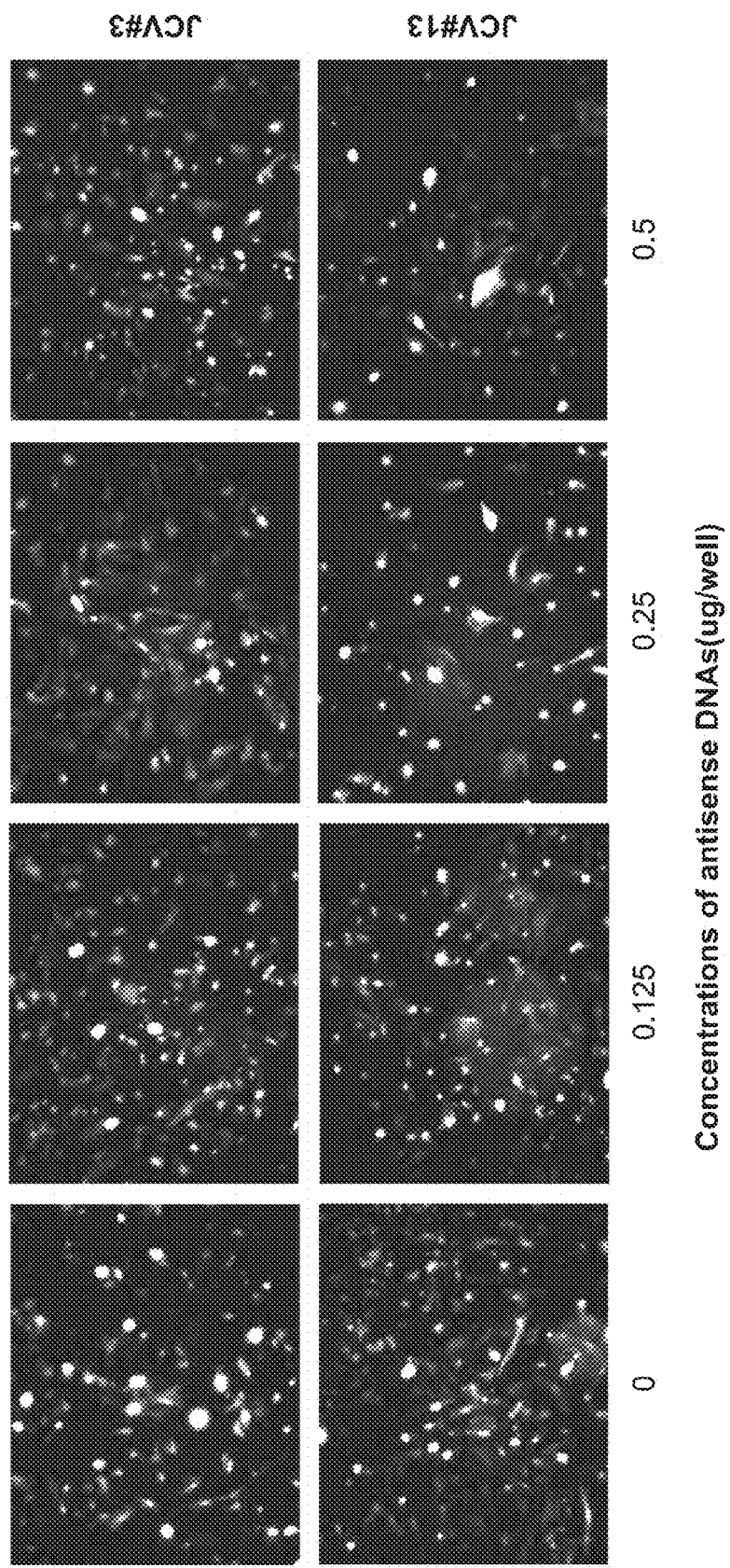

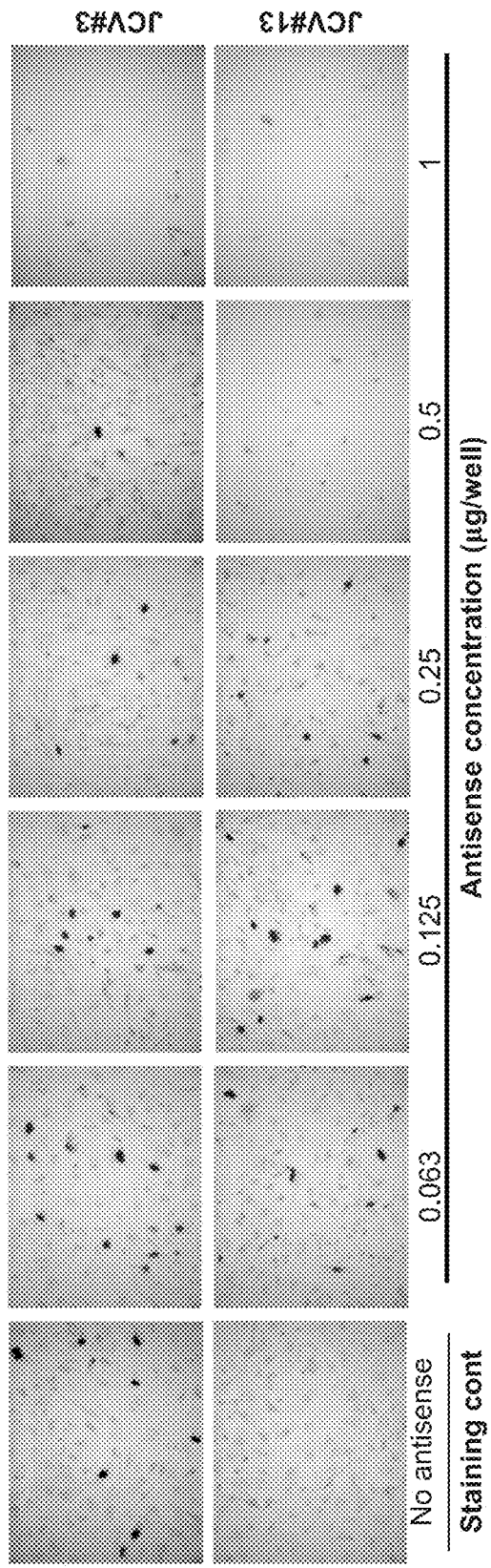
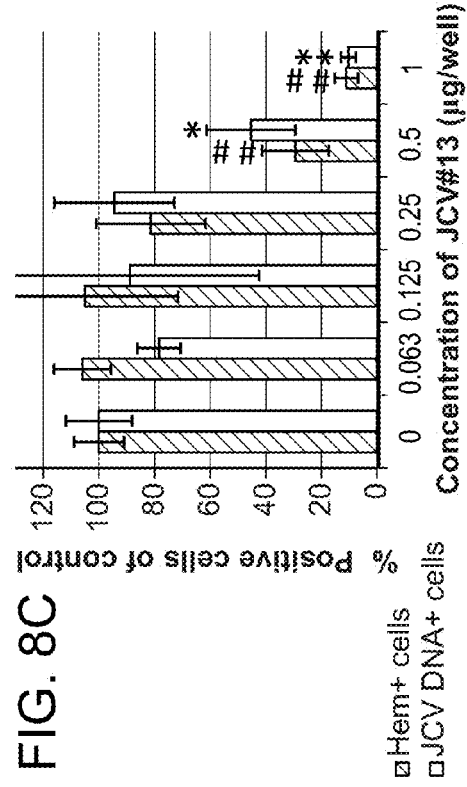
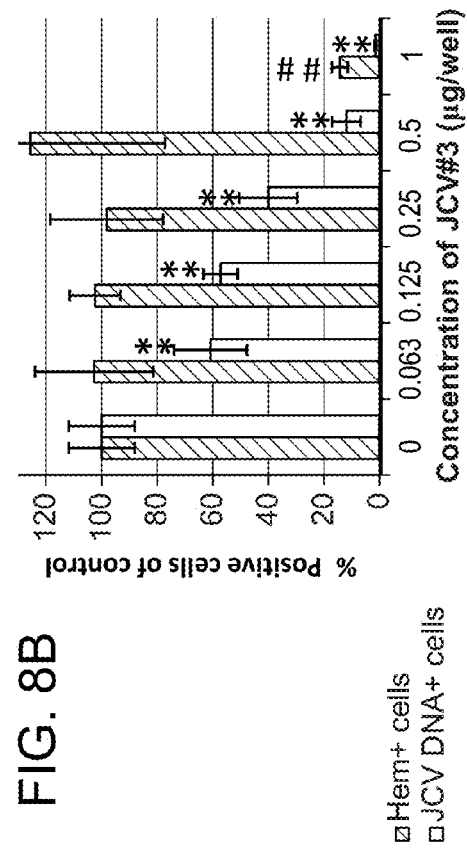
FIG. 8A
FIG. 8B
FIG. 8C

SEQUENCE LISTING

```
<160> NUMBER OF SEQ ID NOS: 33

<210> SEQ ID NO 1
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(21)
<223> OTHER INFORMATION: /note="phosphorothioate bond between
      nucleotides"

<400> SEQUENCE: 1
gttctccaca atctcccagg c                                              21

<210> SEQ ID NO 2
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(20)
<223> OTHER INFORMATION: /note="phosphorothioate bond between
      nucleotides"

<400> SEQUENCE: 2
tctccacaat ctcccaggct                                                20

<210> SEQ ID NO 3
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(21)
<223> OTHER INFORMATION: /note="phosphorothioate bond between
      nucleotides"

<400> SEQUENCE: 3
tctccacaat ctcccaggct t                                              21

<210> SEQ ID NO 4
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: misc_feature
<222> LOCATION: (1)..(21)
<223> OTHER INFORMATION: /note="phosphorothioate bond between
      nucleotides"

<400> SEQUENCE: 4
ttctccacaa tctcccaggc t                                                21

<210> SEQ ID NO 5
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(20)
<223> OTHER INFORMATION: /note="phosphorothioate bond between
      nucleotides"

<400> SEQUENCE: 5
ctccacaatc tcccaggctt                                                  20

<210> SEQ ID NO 6
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(20)
<223> OTHER INFORMATION: /note="phosphorothioate bond between
      nucleotides"

<400> SEQUENCE: 6
ttctccacaa tctcccaggc                                                  20

<210> SEQ ID NO 7
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(21)
<223> OTHER INFORMATION: /note="phosphorothioate bond between
      nucleotides"

<400> SEQUENCE: 7
ctccacaatc tcccaggctt t                                                21

<210> SEQ ID NO 8
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(19)
```

<223> OTHER INFORMATION: /note="phosphorothioate bond between
       nucleotides"

<400> SEQUENCE: 8
ctccacaatc tcccaggct                                                19

<210> SEQ ID NO 9
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"
<220> FEATURE:
<221> NAME/KEY: misc_feature
<222> LOCATION: (1)..(19)
<223> OTHER INFORMATION: /note="phosphorothioate bond between
       nucleotides"

<400> SEQUENCE: 9
tctccacaat ctcccaggc                                                19

<210> SEQ ID NO 10
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"
<220> FEATURE:
<221> NAME/KEY: misc_feature
<222> LOCATION: (1)..(20)
<223> OTHER INFORMATION: /note="phosphorothioate bond between
       nucleotides"

<400> SEQUENCE: 10
gttctccaca atctcccagg                                               20

<210> SEQ ID NO 11
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"
<220> FEATURE:
<221> NAME/KEY: misc_feature
<222> LOCATION: (1)..(20)
<223> OTHER INFORMATION: /note="phosphorothioate bond between
       nucleotides"

<400> SEQUENCE: 11
gtcttcatcc cacttctcat                                               20

<210> SEQ ID NO 12
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic oligonucleotide"
<220> FEATURE:
<221> NAME/KEY: misc_feature
<222> LOCATION: (1)..(21)
<223> OTHER INFORMATION: /note="phosphorothioate bond between
       nucleotides"

<400> SEQUENCE: 12
gtcttcatcc cacttctcat t                                              21

<210> SEQ ID NO 13
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(19)
<223> OTHER INFORMATION: /note="phosphorothioate bond between
      nucleotides"

<400> SEQUENCE: 13
gtcttcatcc cacttctca                                                 19

<210> SEQ ID NO 14
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(21)
<223> OTHER INFORMATION: /note="phosphorothioate bond between
      nucleotides"

<400> SEQUENCE: 14
caggtcttca tcccacttct c                                              21

<210> SEQ ID NO 15
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(20)
<223> OTHER INFORMATION: /note="phosphorothioate bond between
      nucleotides"

<400> SEQUENCE: 15
ggtcttcatc ccacttctca                                                20

<210> SEQ ID NO 16
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(20)
<223> OTHER INFORMATION: /note="phosphorothioate bond between
      nucleotides"

<400> SEQUENCE: 16
gaatccatgg agcttatgga                                                20

<210> SEQ ID NO 17
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(20)
<223> OTHER INFORMATION: /note="phosphorothioate bond between
      nucleotides"

<400> SEQUENCE: 17
agaactccac cctgataaag                                               20

<210> SEQ ID NO 18
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(21)
<223> OTHER INFORMATION: /note="phosphorothioate bond between
      nucleotides"

<400> SEQUENCE: 18
tgcttcaaga gcaggtgtta c                                             21

<210> SEQ ID NO 19
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(15)
<223> OTHER INFORMATION: /note="phosphorothioate bond between
      nucleotides"

<400> SEQUENCE: 19
ttggaacttg cacgg                                                    15

<210> SEQ ID NO 20
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(21)
<223> OTHER INFORMATION: /note="phosphorothioate bond between
      nucleotides"

<400> SEQUENCE: 20
ttctacctct gtaattgagt c                                             21

<210> SEQ ID NO 21

-continued

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(21)
<223> OTHER INFORMATION: /note="phosphorothioate bond between
      nucleotides"

<400> SEQUENCE: 21
ttgtcaacgt atctcatcat g                                              21

<210> SEQ ID NO 22
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(21)
<223> OTHER INFORMATION: /note="phosphorothioate bond between
      nucleotides"

<400> SEQUENCE: 22
gatctgagtt cagagttcca g                                              21

<210> SEQ ID NO 23
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(22)
<223> OTHER INFORMATION: /note="phosphorothioate bond between
      nucleotides"

<400> SEQUENCE: 23
cagtgtgtgt ctgagaagct ca                                             22

<210> SEQ ID NO 24
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: misc_feature
<222> LOCATION: (1)..(1)
<223> OTHER INFORMATION: /note="5' Phos"
<220> FEATURE:
<221> NAME/KEY: misc_feature
<222> LOCATION: (1)..(1)
<223> OTHER INFORMATION: /note="2' O-methyl RNA base"
<220> FEATURE:
<221> NAME/KEY: misc_feature
<222> LOCATION: (2)..(20)
```

<223> OTHER INFORMATION: /note="phosphorothioate bond between
      nucleotides"
<220> FEATURE:
<221> NAME/KEY: misc_feature
<222> LOCATION: (21)..(21)
<223> OTHER INFORMATION: /note="2' O-methyl RNA base"

<400> SEQUENCE: 24
caggtcttca tcccacttct c                                              21

<210> SEQ ID NO 25
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: misc_feature
<222> LOCATION: (1)..(1)
<223> OTHER INFORMATION: /note="2' O-methyl RNA base"
<220> FEATURE:
<221> NAME/KEY: misc_feature
<222> LOCATION: (1)..(20)
<223> OTHER INFORMATION: /note="phosphorothioate bond between
      nucleotides"
<220> FEATURE:
<221> NAME/KEY: misc_feature
<222> LOCATION: (21)..(21)
<223> OTHER INFORMATION: /note="2' O-methyl RNA base"

<400> SEQUENCE: 25
caggtcttca tcccacttct c                                              21

<210> SEQ ID NO 26
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: misc_feature
<222> LOCATION: (1)..(3)
<223> OTHER INFORMATION: /note="2' O-methyl RNA base"
<220> FEATURE:
<221> NAME/KEY: misc_feature
<222> LOCATION: (1)..(20)
<223> OTHER INFORMATION: /note="phosphorothioate bond between
      nucleotides"
<220> FEATURE:
<221> NAME/KEY: misc_feature
<222> LOCATION: (18)..(19)
<223> OTHER INFORMATION: /note="2' O-methyl RNA base"
<220> FEATURE:
<221> NAME/KEY: misc_feature
<222> LOCATION: (21)..(21)
<223> OTHER INFORMATION: /note="2' O-methyl RNA base"

<400> SEQUENCE: 26
caggtcttca tcccactuct c                                              21

<210> SEQ ID NO 27

<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"
<220> FEATURE:
<221> NAME/KEY: misc_feature
<222> LOCATION: (1)..(5)
<223> OTHER INFORMATION: /note="2' O-methyl RNA base"
<220> FEATURE:
<221> NAME/KEY: misc_feature
<222> LOCATION: (1)..(20)
<223> OTHER INFORMATION: /note="phosphorothioate bond between
    nucleotides"
<220> FEATURE:
<221> NAME/KEY: misc_feature
<222> LOCATION: (16)..(19)
<223> OTHER INFORMATION: /note="2' O-methyl RNA base"
<220> FEATURE:
<221> NAME/KEY: misc_feature
<222> LOCATION: (21)..(21)
<223> OTHER INFORMATION: /note="2' O-methyl RNA base"

<400> SEQUENCE: 27
caggucuuca tcccacuuct c                                              21

<210> SEQ ID NO 28
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 28
acagtgtggc cagaattcca ctacc                                          25

<210> SEQ ID NO 29
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 29
taaagcctcc cccccaacag aaa                                            23

<210> SEQ ID NO 30
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 30
agagtgttgg gatcctgtgt ttt                                            23

<210> SEQ ID NO 31
<211> LENGTH: 25
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 31
gagaagtggg gatgaagacc tgttt                                              25

<210> SEQ ID NO 32
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"
<220> FEATURE:
<221> NAME/KEY: misc_feature
<222> LOCATION: (1)..(1)
<223> OTHER INFORMATION: /note="5' 6FAM"
<220> FEATURE:
<221> NAME/KEY: misc_feature
<222> LOCATION: (28)..(28)
<223> OTHER INFORMATION: /note="3' TAMRA"

<400> SEQUENCE: 32
tcatcactgg caaacatttc ttcatggc                                           28

<210> SEQ ID NO 33
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: misc_feature
<222> LOCATION: (1)..(1)
<223> OTHER INFORMATION: /note="2' O-methyl RNA base"
<220> FEATURE:
<221> NAME/KEY: misc_feature
<222> LOCATION: (1)..(21)
<223> OTHER INFORMATION: /note="phosphorothioate bond between
      nucleotides"
<220> FEATURE:
<221> NAME/KEY: misc_feature
<222> LOCATION: (21)..(21)
<223> OTHER INFORMATION: /note="2' O-methyl RNA base"

<400> SEQUENCE: 33
gcgtttgctc ttcttcttgc g                                                  21
```

COMPOSITIONS AND METHODS FOR INHIBITING JC VIRUS (JCV)

CROSS-REFERENCE TO RELATED APPLICATIONS

This application is a national stage application filed under 35 U.S.C. § 371 based on International Application No. PCT/US2014/056655, filed Sep. 19, 2014, which claims priority to, and the benefit under 35 U.S.C. § 119 (e) of, U.S. provisional patent application Ser. No. 61/879,833, filed Sep. 19, 2013, entitled COMPOSITIONS AND METHODS FOR INHIBITING JC VIRUS (JCV). The entire disclosures of the aforementioned patent applications are incorporated herein by this reference.

GOVERNMENT FUNDING

Research supporting this application was carried out by the United States of America as represented by the Secretary, Department of Health and Human Services.

SEQUENCE LISTING

The instant application contains a Sequence Listing which has been submitted electronically in ASCII format and is hereby incorporated by reference in its entirety. Said ASCII copy, created on Mar. 4, 2015, is named 93840WO(47992)_SL.txt and is 13,549 bytes in size.

BACKGROUND OF THE INVENTION

Progressive multifocal leukoencephalopathy (PML) is a rare, fatal demyelinating disease of the brain caused by the polyomavirus JC (JCV) under immunosuppressive conditions. It is pathologically characterized by progressive damage of white matter of the brain by destroying oligodendrocytes at multiple locations. Clinically, PML symptoms include weakness or paralysis, vision loss, impaired speech, and cognitive deterioration. Severe inflammation can result in brain edema and lead herniation and death of the patients (Tan et al., 2009). The prognosis of PML is generally poor. The lifespan for PML patients averaged 9 months for non-AIDS patients and 2 to 4 months for these with HIV infection before antiretroviral drugs were available. The mortality rate of PML is still nearly 50% in HIV-infected patients with antiretroviral therapy (Ferenczy et al., 2012). Although 39% to 58% of the general population are seropositive for antibodies to JCV (Kean et al., 2009, Egli et al., 2009), PML occurs only under immune suppression conditions, such as AIDS patients (Cinque et al., 2009), transplant patients using immunosuppressive medicines (Mateen et al., 2011), certain chemotherapy with immune system damage (Pruitt, 2012), and using natalizumab for multiple sclerosis (Major E. 2010; Sadiq et al., 2010), etc.

No effective therapy for PML has been established, although it is a fatal disease. The current strategies to develop PML therapy focuses on blocking the way of viral infection or the inhibition of JCV replication (Marshall and Major, 2010). Blockage of JCV entry via $5HT_{2A}R$ with receptor antagonists, chlorpromazine and clozapine, effectively inhibited JCV infection (Elphick et al., 2004, Schaumburg et al., 2008, O'Hara et al., 2008, Nukuzuma et al., 2009). Since these are antagonists to other receptors (e.g. dopamine, histamine, adrenergic and acetylcholine receptors) as well, their effect is nonspecific and causes serious side effect and toxicity. Further, although controlled trials have not yet been performed, the clinical efficacy of these compounds seems poor. Several nucleoside analogs, including azidothymidine, acyclovir, CMX001, cidofovir, Ara-A, and Ara-C) have been used for inhibition of JCV replication (Marshall and Major, 2010; Ferenczy et al., 2012). However, these drugs can not only disrupt viral DNA synthesis but cellular DNA synthesis of host as well. With the limited access to the CNS, the therapeutic dose of drug would result in severe side effect in vivo. Anti-inflammatory agents including diclofenac sodium, mefanamic acid and flunixin meglumine, antimalarial drug mefloquine, and the antineoplastic drug isotretinoin have been shown to inhibit JCV replication in vitro. Although mefloquine is the sole drug passing through the blood-brain barrier (Jones et al. 1994; Pham et al. 1999) among these agents, it elicits broad neurotoxicity (Toovry, 2009) and has not shown efficacy in a clinical trial in PML patients (Clifford et al. 2013).

Reports have indicated that in vitro, RNAi may have shown some promise in reducing JC virus replication (Radhakrishnan 2004). However, the RNAi agents examined were not designed against all known JC Virus strains and were not selected for stability and other properties need for in vivo therapeutic RNAi agents. Accordingly, despite significant advances in the field of RNAi, there remains a need for an agent that can selectively and efficiently silence a gene in the JC virus that has both high biological activity and in vivo stability, and that can effectively inhibit replication of the JC virus for use in treating pathological processes mediated by JC virus infection.

SUMMARY OF THE INVENTION

The present invention is based, at least in part, on the development of a treatment option for progressive multifocal leukoencephalopathy (PML). The present invention describes the design of a library of antisense oligodeoxynucleotides (ODNs) that can block polyomavirus JC (JCV) replication and multiplication.

Accordingly, in a first aspect, the present invention provides an antisense oligonucleotide which is targeted to a nucleic acid encoding polyomavirus JC (JCV), and is capable of inhibiting JCV replication and multiplication.

In another aspect, the invention features an antisense oligonucleotide comprising a phosphorothioate backbone, wherein the oligonucleotide is targeted to a nucleic acid encoding polyomavirus JC (JCV), and is capable of inhibiting JCV replication or multiplication.

In one embodiment, the oligonucleotide comprises at least one backbone modification. In another embodiment, the backbone modification is a phosphorothioate modification. In a further related embodiment, the backbone comprises a methylribose modification.

In another embodiment, the oligonucleotide further comprises at least one 2' sugar modification.

In one embodiment of the above aspect, the oligonucleotide is targeted to a first nucleic acid coding region of early proteins that are expressed before viral replication, a second nucleic acid coding region of late proteins that are expressed after the onset of viral replication, or a third nucleic acid hypervariable regulatory region in between the first and the second regions.

In another embodiment, the early proteins that are expressed before viral replication are selected from the group consisting of large T antigen (T-Ag), small t antigen (t-Ag), and mRNA splicing products T' 135, T' 136, T' 165.

In another embodiment, the late proteins that are expressed after the onset of viral replication are selected from the group consisting of: capsid protein VP1, capsid protein VP2, capsid protein VP3, and an accessory agnoprotein.

In still another embodiment, the hypervariable regulatory region comprises an origin of DNA replication and promoters for early and late transcription.

In another embodiment of the above aspects, the antisense oligonucleotide comprises a nucleic acid sequence at least 85% identical to a nucleic acid sequence selected from the group consisting of: SEQ ID NO: 1, 2, 3, 4, 5, 6, 7, 8, 9, 10, 11, 12, 13, 14, 15, 16, 17, 18, 19, 20, 21, 22 and 23.

In another embodiment of the above aspects, the antisense oligonucleotide consists of a nucleic acid sequence selected from the group consisting of: SEQ ID NO: 1, 2, 3, 4, 5, 6, 7, 8, 9, 10, 11, 12, 13, 14, 15, 16, 17, 18, 19, 20, 21, 22 and 23.

The invention also features a pharmaceutical composition comprising one or more oligonucleotides of the above aspects, and a pharmaceutical carrier.

In another aspect, the invention features a method of inhibiting JCV replication or multiplication in a subject, comprising administering to the subject the pharmaceutical composition of the above aspects and embodiment.

In another aspect, the invention features a method of treating a subject having or at risk for having progressive multifocal leukoencephalopathy (PML), comprising administering to the subject an effective amount of the pharmaceutical composition of claim 13, thereby treating PML.

In still another aspect, the invention features a method of preventing PML in a subject having or at risk for having PML, comprising administering to the subject an effective amount of the pharmaceutical composition of the above aspects and embodiments, thereby preventing PML.

In one embodiment of the above aspects, the subject is an immunosuppressed or immunocompromised subject.

In another embodiment of the above aspects, the method further comprises administration of an additional agent.

In another embodiment of the above aspects, the invention features a kit comprising one or more oligonucleotides of the above aspects and embodiments.

In one embodiment, the kit further comprises instructions for use for inhibiting JCV replication or multiplication.

Other aspects of the invention are described in, or are obvious from, the following disclosure, and are within the ambit of the invention.

BRIEF DESCRIPTION OF THE DRAWINGS

For a fuller understanding of the present disclosure, reference is made to the following detailed description taken in conjunction with the accompanying drawing figures wherein:

FIG. 8 shows suppressed replication of JCV in Mad 4 infected PDA cells by $JCV^{\#}3$ but not $JCV^{\#}13$. PDA cells were infected with 200 HAu per 1 million cells, then transfected the next day with 0, 0.06, 0.13, 0.25 0.50 and 1.00 ug/well of $JCV^{\#}3$ and $JCV^{\#}13$, and cultured for 15 more days. At the end, the cells were fixed and analyzed by in situ hybridization and counter-stained with hematoxilyn. (A) Image of in situ hybridization under DIC. The dark brown precipitation in the nuclei of the infected PDA cells is representative of the de novo-synthesis of JCV-DNA. (B) and (C) demonstrated quantitative analyses of toxicity (blue bar) and efficacy (brown bar) of $JCV^{\#}3$ and $JCV^{\#}13$, respectively. Data are representative of 5 randomly counted photo areas and are expressed as percentages of the JCV-infected, non-antisense-control value±standard deviations (SD). Statistical analysis was carried out with ANOVA assay followed by Tukey HSD Test at significant level of 0.01. * P<0.05 and ** P<0.01 comparing with control of JCV-infected alone in efficacy evaluation; ## P<0.01 comparing with control of JCV-infected alone in cytotoxic evaluation.

DETAILED DESCRIPTION OF THE INVENTION

Figure 1A:
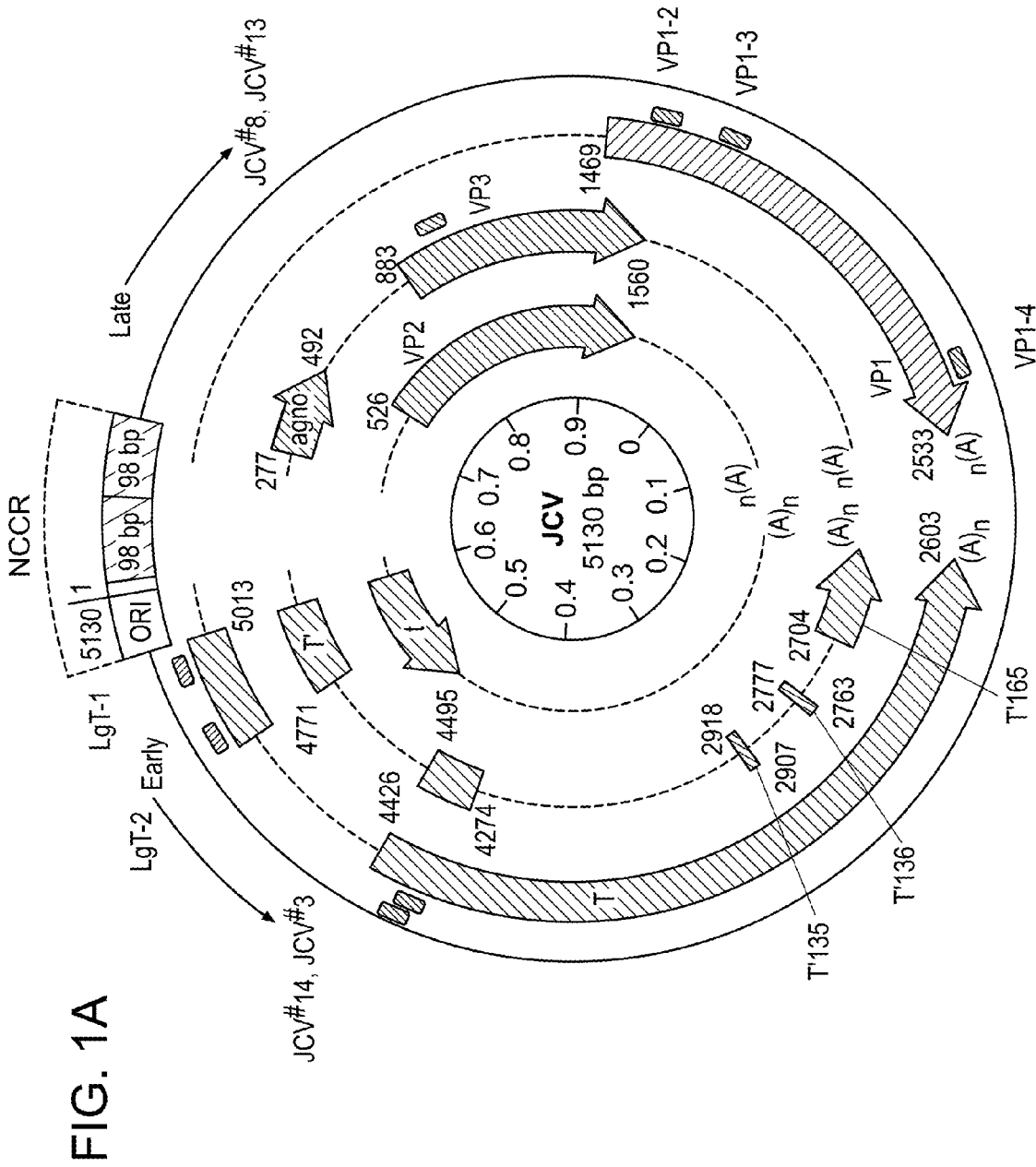
FIG. 1 shows JCV genomic regions aligned with antisense DNAs used in this study. (A) Alignment of tested antisense DNAs in reference to a circular map of the JCV genome. (B) Detailed information of the antisense DNAs, including the nucleotide (nt) length, the protein targets and homology with the different JCV regions in its genome diagram.

The instant invention describes the design of antisense ODNs that are single strand DNA molecules, and that can block replication of JCV. Previous studies have shown that unmodified oligonucleotides are degraded rapidly in biologic fluids by nucleases. Therefore, to decrease the likelihood that the ODNs of the present invention would be recognized and degraded, the ODNs were modified to contain a phosphorothioate backbone (PS-ODN). In addition to the PS-ODNs, the present invention also describes mixed backbone ODNs that contain the PS-ODN backbone with an additional modification designed to increase stability, the 2'-O-methyl-ribose (Dias and Stein, 2002). Further studies indicate that administration of a "cocktail" (e.g. one or more, two or more . . . ten or more, etc.) of PS-ODNs directed at different targets within the mRNA is more effective than administration of individual PS-ODNs. Accordingly, the present invention describes PS-ODNs directed towards different regions of the JCV mRNA sequence which can be administered as an antisense cocktail or as individual agents.

Definitions

The following definitions will be useful in understanding the instant invention.

As used herein, the term "comprising" is intended to mean that the compositions and methods include the recited elements, but do not exclude other elements. "Consisting essentially of", when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

As used in the specification and claims, the singular form "a", "an" and "the" include plural references unless the context clearly dictates otherwise.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

Unless specifically stated or obvious from context, as used herein, the term "or" is understood to be inclusive.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

As used herein, the term "administering" is meant to refer to a means of providing the composition to the subject in a manner that results in the composition being inside the subject's body. Such an administration can be by any route including, without limitation, subcutaneous, intradermal, intravenous, intra-arterial, intraperitoneal, and intramuscular.

As used herein, the term "agent" refers to any molecule that can be administered in addition to the antisense ODNs of the present invention. In exemplary embodiments, such an agent will be a "therapeutic agent" capable of exerting an effect on a target, in vitro or in vivo. Exemplary agents include, for example, prodrugs, diagnostic agents, imaging agents, therapeutic agents, chemotherapeutic agents, pharmaceutical agents, drugs, synthetic organic molecules, proteins, peptides, vitamins, and steroids.

As used herein the term "antisense" is meant to refer to the relationship between an oligonucleotide and its complementary target. The oligonucleotides are able to inhibit the function of RNA; either its translation into protein, its translocation into the cytoplasm, maturation, or any other activity necessary to its overall biological function. The failure of the RNA to perform all or part of its function results in failure of a portion of the genome controlling the normal life cycle of the virus.

As used herein, a "composition" refers to an active agent (e.g., antisense ODNs). The composition additionally can comprise a pharmaceutically acceptable carrier or excipient and/or one or more therapeutic agents for use in vitro or in vivo.

As used herein, the term "effective amount" refers to that amount of a therapeutic agent alone that produces the desired effect (such as treatment of a medical condition such as PML) in a patient. In some aspects, the phrase refers to an amount of therapeutic agent that, when incorporated into a composition of the invention, provides a preventative effect sufficient to prevent or protect an individual from future medical risk associated with a particular disease or disorder, such as PML. A physician or veterinarian of ordinary skill can readily determine and prescribe the effective amount of the bioactive agent required to treat and/or prevent the progress of the condition.

As used herein, "kits" are understood to contain at least the non-standard laboratory reagents of the invention and one or more non-standard laboratory reagents for use in the methods of the invention.

As used herein, the term "oligonucleotide" is meant to refer to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Modified or substituted oligonucleotides may be preferred over native forms because of desirable properties such as, for example, enhanced cellular uptake, enhanced affinity for nucleic acid target and increased stability in the presence of nucleases. A discussion of antisense oligonucleotides and some desirable modifications can be found in De Mesmaeker et al. 1995, incorporated by reference in its entirety herein.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin *Remington's Pharm. Sci.,* 15th Ed. (Mack Publ. Co., Easton, 1975).

As used herein, "phosphorothioate" are meant to refer to a variant of normal DNA in which one of the non-bridging oxygen molecules is replaced by sulfur.

As used herein, the term "replication" is meant to refer to the duplication of the viral genome.

As used herein, the term "multiplication" is meant to refer to the making of a new viral organism (e.g. multiplication of one virus to 1000)

As used herein, the term "subject" is intended to include organisms needing treatment. Examples of subjects include mammals, e.g., humans, dogs, cows, horses, pigs, sheep, goats, cats, mice, rabbits, rats, and transgenic non-human animals. In certain embodiments, the subject is a human.

As used herein, the term "treated," "treating" or "treatment" includes the diminishment or alleviation of at least one symptom associated or caused by the state, disorder or disease being treated, for example PML. A subject that has been treated can exhibit a partial or total alleviation of symptoms, or symptoms can remain static following treatment according to the invention. The term "treatment" is intended to encompass prophylaxis, therapy and cure.

Other definitions appear in context throughout the disclosure.

JCV Antisense Oligodeoxynucleotides (ODNs)

Antisense oligodeoxynucleotides (ODNs) are short nucleic acids that are used to alter protein expression in a highly specific yet simple manner. The relationship between an oligonucleotide and its complementary target is commonly denoted as antisense. The oligonucleotides are able to inhibit the function of RNA; either its translation into protein, its translocation into the cytoplasm, maturation, or any other activity necessary to its overall biological function.

Progressive multifocal leukoencephalopathy (PML) is a relatively rare and commonly fatal viral disease characterized by progressive damage, with occasional inflammation of the white matter of the brain at multiple locations. It occurs most frequently in people with severe immune deficiency, for example, but not limited to transplant patients on immunosuppressive medications, those receiving certain kinds of chemotherapy and those with AIDS.

JCV, the etiologic agent for PML, is normally present and kept under control by the immune system. JCV is a double-stranded DNA virus with 5,130 base pairs (bp) of nucleotides in length. In genomic structure, JCV can be divided into three functional areas, including coding region of early proteins that express before viral replication, coding region of late proteins that express after the onset of viral replication and a hypervariable regulatory region in between, composed of an origin of DNA replication and the promoters for early and late transcriptions.

Figure 2B:
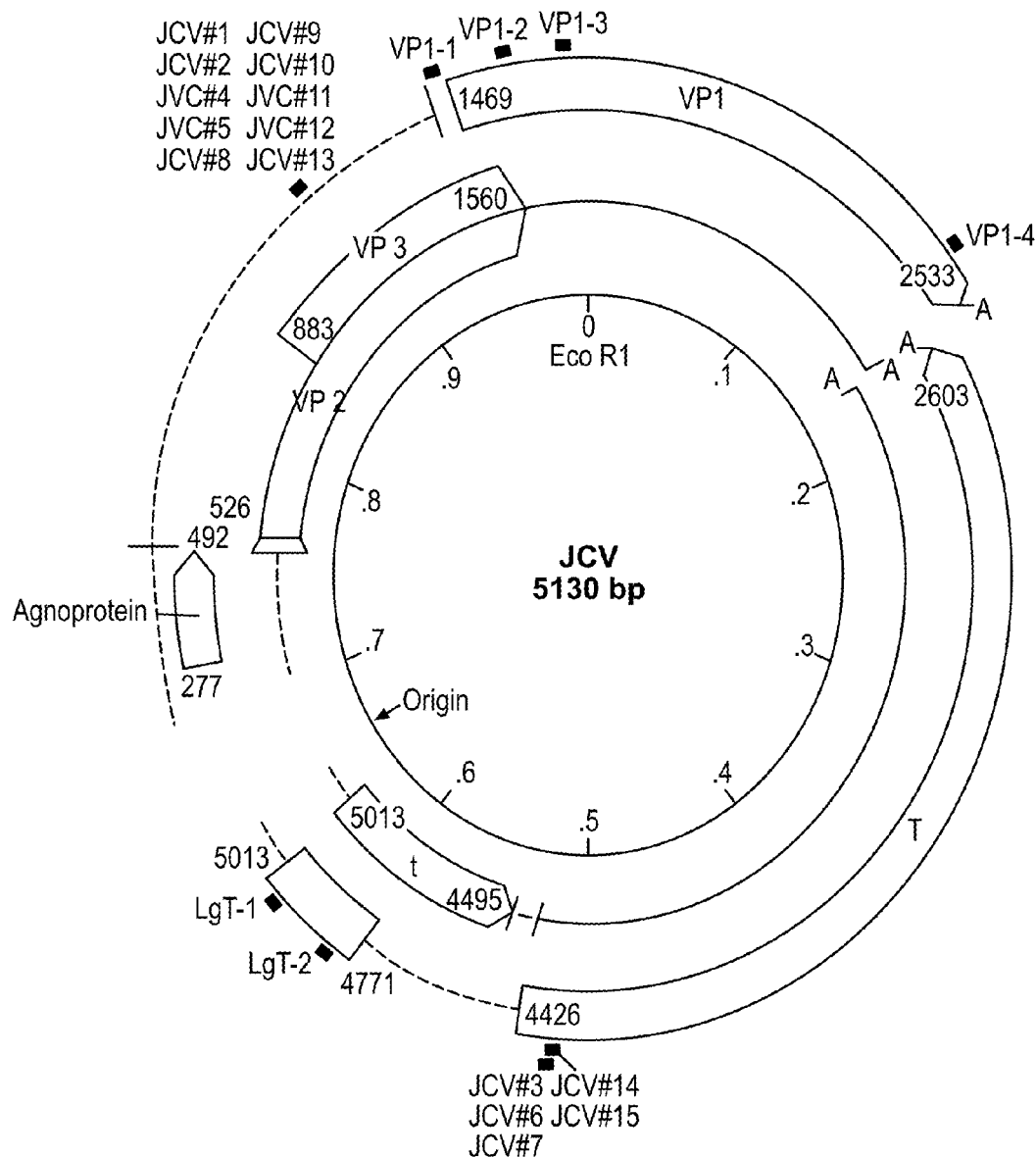
FIG. 2 shows the specific sequences of all the antisense DNAs and their position in the JCV genome map.
FIG. 2A discloses SEQ ID NOS 1-10, 16-17, and 11-15, respectively, in order of appearance, and FIG. 2B discloses SEQ ID NOS 18-23 and 33, respectively, in order of appearance.

A schematic of the JCV genomic structure is shown in FIG. 2, with report of the entire viral genome nucleotide sequence in Frisque et al 1984.

The early and late mRNAs are transcribed in opposite directions. The early proteins include large T antigen (T-Ag) and small t antigen (t-Ag), as well as 3 additional different mRNA splicing products T' 135, T' 136, T' 165. T-Ag could bind to the regulatory region and initiate viral replication by diverse mechanisms and t-Ag is also involved in the process of viral replication via binding to host PP2A and pRb proteins (Bollag et al, 2010). The coding region of late proteins could transcript capsid proteins VP1, VP2 and VP3, and an accessory agnoprotein. The agnoprotein is a regulatory protein, and its function is not well understood. The latest research revealed that it may be involved in viral DNA replication by affecting T-Ag binding to the viral origin (Saribas et al, 2012), early and late gene expressions (Okada et al., 2001), stabilizing the viral three-dimensional structure (Suzuki et al., 2012), acting as a viroporin (Suzuki et al., 2010), and inducing host cell death (Merabova et al., 2008). JCV can cross the blood-brain barrier into the central nervous system (CNS), where it infects oligodendrocytes and astrocytes. VP1 is the sole JCV protein that exposes on the surface of the capsid (Ferenczy et al., 2012), with key role in interaction with serotonin receptor 5HT2AR and sialic acid-containing receptors on the glial cells for viral infection (Elphick et al., 2004, Dugan et al., 2008), while VP2 and VP3 are minor capsid proteins with a function of retaining VP1 in the nucleus of host cell for virion assemble (Shishido-Hara et al, 2004).

In certain embodiments, the antisense oligonucleotides that are capable of inhibiting JCV replication as described herein are targeted to a first nucleic acid coding region of early proteins that are expressed before viral replication, a second nucleic acid coding region of late proteins that are expressed after the onset of viral replication, or a third nucleic acid hypervariable regulatory region in between the first and the second regions.

In one embodiment, the early proteins that are expressed before viral replication are selected from the group consisting of large T antigen (T-Ag), small t antigen (t-Ag), and mRNA splicing products T' 135, T' 136, T' 165. This region of the viral genome is termed the early region starting at nucleotide 5113.

In another embodiment, the late proteins that are expressed after the onset of viral replication are selected from the group consisting of capsid protein VP1, capsid protein VP2, capsid protein VP3, and an accessory agnoprotein. This region of the viral genome is termed LATE starting at nucleotide 207.

In another embodiment, the hypervariable regulatory region comprises an origin of DNA replication and promoters for early and late transcription. This region of the viral genome is termed Non Coding Regulatory Region or NCRR starting at nucleotide 11 to nucleotide 206.

In accordance with the present invention, antisense oligonucleotides are targeted to a nucleic acid encoding JCV, and are capable of inhibiting JCV replication are provided. The nucleic acid targets may be DNA, RNA, or pre-RNA. "Targeting" an oligonucleotide to a selected nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a foreign nucleic acid from an infectious agent. In the present invention, the target is a JCV gene or mRNA transcribed from a JCV gene. The targeting process also includes determination of a site or sites within this gene for the oligonucleotide interaction to occur such that the desired effect, either detection or modulation of expression of the protein, will result. Once the target site has been identified, oligonucleotides are chosen which are sufficiently complementary to the target, i.e., hybridize sufficiently well and with sufficient specificity, to give the desired effect. "Hybridization", in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them.

An antisense compound is specifically hybridizable when binding of the compound to the target nucleic acid interferes with the normal function of the target nucleic acid to cause a loss of activity, and there is a sufficient degree of complementarity to avoid nonspecific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an antisense compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure or hairpin structure). It is preferred that the antisense compounds of the present invention comprise at least 70%, or at least 75%, or at least 80%, or at least 85% sequence complementarity to a target region within the target nucleic acid, more preferably that they comprise at least 90% sequence complementarity and even more preferably comprise at least 95% or at least 99% sequence complementarity to the target region within the target nucleic acid sequence to which they are targeted. For example, an antisense compound in which 18 of 20 nucleobases of the antisense compound are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al. 1990; Zhang and Madden 1997).

Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). In some preferred embodiments, homology, sequence identity or complementarity, between the oligomeric and target is between about 50% to about 60%. In some embodiments, homology, sequence identity or complementarity, is between about 60% to about 70%. In preferred embodiments, homology, sequence identity or complementarity, is between about 70% and about 80%. In more preferred embodiments, homology, sequence identity or complementarity, is between about 80% and about 90%. In some preferred embodiments, homology, sequence identity or complementarity, is about 90%, about 92%, about 94%, about 95%, about 96%, about 97%, about 98%, about 99% or about 100%

Accordingly, in one embodiment, the antisense oligonucleotides comprise a nucleic acid sequence at least 85% identical to a nucleic acid sequence selected from the group consisting of: SEQ ID NO: 1, 2, 3, 4, 5, 6, 7, 8, 9, 10, 11, 12, 13, 14, 15, 16, 17, 18, 19, 20, 21, 22 and 23. In one embodiment, the antisense oligonucleotides comprise a nucleic acid sequence at least 90%, 91%, 92%, 93%, 94%, 95%, 96%, 97%, 98% or 99% identical to a nucleic acid sequence selected from the group consisting of: SEQ ID NO: 1, 2, 3, 4, 5, 6, 7, 8, 9, 10, 11, 12, 13, 14, 15, 16, 17, 18, 19, 20, 21, 22 and 23.

In another embodiment, the antisense oligonucleotides consist of a nucleic acid sequence selected from the group consisting of: SEQ ID NO: 1, 2, 3, 4, 5, 6, 7, 8, 9, 10, 11, 12, 13, 14, 15, 16, 17, 18, 19, 20, 21, 22 and 23.

SEQ ID NOs 1-23 are shown below. * represents phosphorothioate bonds.

(JCV#1)

SEQ ID NO: 1

5'-G*T*T* C*T*C* C*A*C* A*A*T* C*T*C* C*C*A*

G*G*C-3'

(JCV#2)

SEQ ID NO: 2

5'-T* C*T*C* C*A*C* A*A*T* C*T*C* C*C*A*

G*G*C*T-3'

(JCV#4)

-continued

SEQ ID NO: 3
5'-T* C*T*C* C*A*C* A*A*T* C*T*C* C*C*A* G*G*C*T*T-3'
(JCV#5)

SEQ ID NO: 4
5'-T*T* C*T*C* C*A*C* A*A*T* C*T*C* C*C*A* G*G*C*T-3'
(JCV#8)

SEQ ID NO: 5
5'-C*T*C* C*A*C* A*A*T* C*T*C* C*C*A* G*G*C*T*T-3'
(JCV#9)

SEQ ID NO: 6
5'-T*T* C*T*C* C*A*C* A*A*T* C*T*C* C*C*A* G*G*C-3
(JCV#10)

SEQ ID NO: 7
5'-C*T*C* C*A*C* A*A*T* C*T*C* C*C*A* G*G*C*T*T-3'
(JCV#11)

SEQ ID NO: 8
5'-C*T*C* C*A*C* A*A*T* C*T*C* C*C*A* G*G*C*T-3'
(JCV#12)

SEQ ID NO: 9
5'-T* C*T*C* C*A*C* A*A*T* C*T*C* C*C*A* G*G*C-3'
(JCV#13)

SEQ ID NO: 10
5'-G*T*T* C*T*C* C*A*C* A*A*T* C*T*C* C*C*A* G*G-3'
(JCV#3)

SEQ ID NO: 11
5'-G*T*C* T*T*C* A*T*C* C*C*A* C*T*T* C*T*C* A*T-3'
(JCV#6)

SEQ ID NO: 12
5'-G*T*C* T*T*C* A*T*C* C*C*A* C*T*T* C*T*C* A*T*T-3'
(JCV#7)

SEQ ID NO: 13
5'-G*T*C* T*T*C* A*T*C* C*C*A* C*T*T* C*T*C* A-3'
(JCV#14)

SEQ ID NO: 14
5'-C*A*G*G*T*C* T*T*C* A*T*C* C*C*A* C*T*T* C*T*C-3'
(JCV#15)

SEQ ID NO: 15
5'-G*G*T*C* T*T*C* A*T*C* C*C*A* C*T*T* C*T*C*A-3'
(LgT-1)

SEQ ID NO: 16
5'-G*A*A*T*C*C*A*T*G*G*A*G*C*T*T*A*T*G*G*A-3'
(LgT-2)

SEQ ID NO: 17
5'-A*G*A*A*C*T*C*C*A*C*C*C*T*G*A*T*A*A*A*G-3'
(Vp1-1)

SEQ ID NO: 18
5'-T*G*C*T*T*C*A*A*G*A*G*C*A*G*G*T*G*T*T*A*C-3'
(Vp1-2)

SEQ ID NO: 19
5'-T*T*G*G*A*A*C*T*T*G*C*A*C*G*G-3'
(Vp1-3)

SEQ ID NO: 20
5'-T*T*C*T*A*C*C*T*C*T*G*T*A*A*T*T*G*A*G*T*C-3'
(Vp1-4)

SEQ ID NO: 21
5'-T*T*G*T*C*A*A*C*G*T*A*T*C*T*C*A*T*C*A*T*G-3'
(Scram 1)

SEQ ID NO: 22
5'-G*A*T*C*T*G*A*G*T*T*C*A*G*A*G*T*T*C*C*A*G-3'
(Scram 3)

SEQ ID NO: 23
5'-C*A*G*T*G*T*G*T*G*T*C*T*G*A*G*A*A*G*C*T*C*A-3'

The oligonucleotides and analogs used in accordance with this invention may be conveniently and routinely made through the well-known technique of solid phase synthesis. Equipment for such synthesis is sold by several vendors including Applied Biosystems. Any other means for such synthesis may also be employed, however, the actual synthesis of the oligonucleotides are well within the knowledge of one skilled in the art.

Modifications

Specific examples of some preferred oligonucleotides envisioned for this invention include those containing modified backbones, for example, phosphorothioate. In one aspect, the invention features an antisense oligonucleotide comprising a phosphorothioate backbone, wherein the oligonucleotide is targeted to a nucleic acid encoding polyomavirus JC (JCV), and is capable of inhibiting JCV replication. In further embodiments, the phosphorothioate is modified with methylribose.

Other modifications may include phosphotriesters, methyl phosphonates, short chain alkyl or cycloalkyl intersugar linkages or short chain heteroatomic or heterocyclic intersugar linkages. Exemplary oligonucleotides with phosphorothioate backbones and those with heteroatom backbones include $CH_2$—NH—O—$CH_2$, $CH_2$—N($CH_3$)—O—$CH_2$ [known as a methylene (methylimino) or MMI backbone], $CH_2$—O—N($CH_3$)—$CH_2$, $CH_2$—N($CH_3$)—N($CH_3$)—$CH_2$ and O—N(CH3)-$CH_2$—$CH_2$ backbones, wherein the native phosphodiester backbone is represented as O—P—O—$CH_2$. The amide backbones disclosed by De Mesmaeker et al. 1995) are also contemplated. In other embodiments, the backbone modification is a peptide nucleic acid modification.

Oligonucleotides of the present invention may also contain one or more substituted sugar moieties. For example, oligonucleotides may comprise one of the following at the 2' position: OH, SH, $SCH_3$, F, OCN, $OCH_3$ $OCH_3$, $OCH_3$ $O(CH_2)_n$ $CH_3$, $O(CH_2)_n NH_2$ or $O(CH_2)$ n $CH_3$ where n is from 1 to about 10; C1 to C10 lower alkyl, alkoxyalkoxy (i.e., —O— alkyl-O-alkyl), substituted lower alkyl, alkaryl or aralkyl; Cl; Br; CN; $CF_3$; $OCF_3$; O—, S—, or N-alkyl; O—, S—, or N-alkyl; O-, S-, or N-alkenyl; $SOCH_3$; $SO_2$ $CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—CH$_2$ CH$_2$ OCH$_3$, also known as 2'-O- (2-methoxyethyl)] (Martin et al. Helv. Chim Acta 1995, 78, 486). Other preferred modifications include 2'-methoxy 2'-propoxy (2'-OCH$_2$ CH$_2$ CH$_3$) and 2'-fluoro (2'—F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-me pyrimidines, particularly 5-methylcytosine (also referred to as 5-methyl-2'deoxycytosine and often referred to in the art as 5-me-C), 5-hydroxymethylcytosine (HMC), glycosyl HMC and gentobiosyl HMC, as well as synthetic nucleobases, e.g., 2-aminoadenine, 2-thiouracil, 2-thiothymine, 5-bromouracil, 5-hydroxymethyluracil, 8-azaguanine, 7-deazaguanine, N.sup. 6 (6-aminohexyl)adenine and 2,6-diaminopurine. Kornberg, A. DNA Replication, W.H. Freeman & Co., San Francisco, 1980, pp 75-77; Gebeyehu, G., et al. Nucl. Acids Res. 1987, 15, 4513). A "universal" base known in the art, e.g., inosine, may be included. 5-me-C substitutions have been shown to increase nucleic acid duplex stability by 0.6-1.2° C. (Sanghvi, Y. S. in Antisense Research and Applications, Crooke and Lebleu, eds., CRC Press, Boca Raton, 1993, pp. 276-278) and are presently preferred base substitutions.

Another modification of the antisense compounds of the invention involves chemically linking to the antisense compound one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, and groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860, the entire disclosure of which are incorporated herein by reference. Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Antisense compounds of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety. The oligonucleotides of the invention may be provided as prodrugs, which comprise one or more moieties which are cleaved off, generally in the body, to yield an active oligonucleotide. One example of a prodrug approach is described by Imbach et al. in WO Publication 94/26764.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides. "Chimeric" oligonucleotides are oligonucleotides which contain two or more chemically distinct regions, each made up of at least one nucleotide. These oligonucleotides contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Consequently, comparable results can often be obtained with shorter oligonucleotides when chimeric oligos are used, compared to phosphorothioate deoxyoligonucleotides hybridizing to the same target region. Cleavage of the RNA target can be routinely detected by gel electrophoresis and, if necessary, associated nucleic acid hybridization techniques known in the art. Typically, chimeric oligonucleotides are "gapped" oligonucleotides (or "gapmers") in which a region of deoxynucleotides (the "gap"), preferably containing at least four contiguous deoxynucleotides, is flanked by regions of modified nucleotides, preferably 2'-sugar modified nucleotides. In a preferred embodiment, the flanking regions (or "wings") contain 2'-alkoxy or 2'alkoxyalkoxy modifications, more preferably 2'-methoxyethoxy. In preferred embodiments the backbone may be phosphorothioate throughout or may be phosphodiester in the "wings" and phosphorothioate in the "gap". In other preferred embodiments, chimeric oligonucleotides may be "winged" oligonucleotides (or "wingmers" or hemichimeras) in which there is a deoxy "gap", preferably at least 4 contiguous deoxynucleotides, flanked on either the 5' or the 3' side by a region of modified nucleotides. Again, the flanking region (or "wing") preferably contains 2'-alkoxy or 2'alkoxyalkoxy modifications, more preferably 2'-methoxyethoxy, and the backbone may be phosphorothioate throughout or may be phosphodiester in the "wing" and phosphorothioate in the "gap". Other configurations of chimeric oligonucleotide are also comprehended by this invention. These may involve other modifications of the sugar, base or backbone, preferably in the oligonucleotide wing(s).

Screening and Target Validation

The antisense oligonucleotides of the present invention are targeted to a nucleic acid encoding polyomavirus JC (JCV). The target segments identified herein may be employed in a screen for additional compounds that modulate the replication of JCV. The screening method comprises the steps of contacting a preferred target segment of a nucleic acid molecule encoding JCV with one or more candidate modulators, and selecting for one or more candidate modulators which inhibit JCV replication. Once it is shown that the candidate modulator or modulators are capable of modulating JCV expression, the modulator may then be employed in further investigative studies of the JCV, or for use as a research, diagnostic, or therapeutic agent in accordance with the present invention.

The preferred target segments of the present invention may be also be combined with their respective complementary antisense compounds of the present invention to form stabilized double-stranded (duplexed) oligonucleotides. Such double stranded oligonucleotide moieties have been shown in the art to modulate target expression and regulate translation as well as RNA processing via an antisense mechanism. Moreover, the double-stranded moieties may be subject to chemical modifications (Fire et al., Nature, 1998, 391, 806-811; Timmons and Fire, Nature 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev. 2001, 15, 188-200). For example, such double-stranded moieties have been shown to inhibit the target by the classical hybridization of antisense strand of the duplex to the target, thereby triggering enzymatic degradation of the target (Tijsterman et al., Science, 2002, 295, 694-697).

The antisense compounds of the present invention can also be applied in the areas of drug discovery and target validation. The present invention comprehends the use of the compounds and preferred target segments identified herein in drug discovery efforts to elucidate relationships that exist between JCV and a disease state, phenotype, or condition, for example PML. These methods include detecting or modulating JCV replication comprising contacting a sample, tissue, cell, or organism with the compounds of the present invention, measuring the JCV replication and/or a related phenotypic or chemical endpoint at some time after treatment, and optionally comparing the measured value to a non-treated sample or sample treated with a further compound of the invention.

Compositions

The invention, in part, pertains to pharmaceutical compositions comprising one or more oligonucleotides or modified oligonucleotides which is targeted to a nucleic acid encoding polyomavirus JC (JCV) and a pharmaceutical carrier.

In preferred embodiments, the oligonucleotides of the present invention are administered in a cocktail of one or more different oligonucleotides. For example, combination of JCV#14 with VP-1-3.

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof. The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells. Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety. In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration. Alternative routes of administration would include intrathecal injection and/or use of a pump, convection enhanced delivery with use of a pump, intravenous, intranasal, or parenteral.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315,298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein in its entirety. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligonucleotides and their preparation are described in detail in U.S. application Ser. No. 09/108,673 (filed Jul. 1, 1998), Ser. No. 09/315,298 (filed May 20, 1999) and Ser. No. 10/071,822, filed Feb. 8, 2002, each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligonucleotide which is targeted to a nucleic acid encoding polyomavirus JC (JCV) and one or more other agents, for example any agent which functions by a non-antisense mechanism, preferably a therapeutic agent.

The therapeutic agent is selected from, but not limited to chemotherapeutic agents, cardiovascular drugs, respiratory drugs, sympathomimetic drugs, cholinomimetic drugs, adrenergic or adrenergic neuron blocking drugs, analgesics/antipyretics, anesthetics, antiasthmatics, antibiotics, antidepressants, antidiabetics, antifungals, antihypertensives, anti-inflammatories, antianxiety agents, immunosuppressive agents, immunomodulatory agents, antimigraine agents, sedatives/hypnotics, antianginal agents, antipsychotics, antimanic agents, antiarrhythmics, antiarthritic agents, antigout agents, anticoagulants, thrombolytic agents, antifibrinolytic agents, hemorheologic agents, antiplatelet agents, anticonvulsants, antiparkinson agents, antihistamines/antipruritics, agents useful for calcium regulation, antibacterials, antivirals, antimicrobials, anti-infectives, bronchodialators, hormones, hypoglycemic agents, hypolipidemic agents, proteins, peptides, nucleic acids, agents useful for erythropoiesis stimulation, antiulcer/antireflux agents, antinauseants/antiemetics and oil-soluble vitamins, or combinations thereof.

The composition comprising the oligonucleotides and the agent are administered simultaneously, either in the same composition or in separate compositions. In some embodiments, the oligonucleotide composition and the second therapeutic agent are administered sequentially, i.e., the oligonucleotide composition is administered either prior to or after the administration of the agent. The term "sequential administration" as used herein means that the oligonucleotide and the second agent are administered with a time separation of more than about 15 minutes, such as more than about any of 20, 30, 40, 50, 60 or more minutes. Either may be administered first. The composition and the chemotherapeutic agent are contained in separate compositions, which may be contained in the same or different packages. In some embodiments, the administration of the oligonucleotide composition and the agent are concurrent, i.e., the administration period of the oligonucleotide composition and that of the second agent overlap with each other. In some embodiments, the administration of the oligonucleotide composition and the agent are non-concurrent.

Methods of Treatment

The methods of the invention encompass methods of treating or preventing diseases or disorders by administering to subjects in need thereof an effective amount of an antisense ODN as described herein.

In certain aspects, the invention features methods of inhibiting JCV replication in a subject, comprising administering to the subject the pharmaceutical composition comprising the antisense ODNs described herein.

The invention also features methods of treating a subject having or at risk for having progressive multifocal leukoencephalopathy (PML), comprising administering to the subject an effective amount of the pharmaceutical composition comprising the antisense ODNs described herein.

The invention also features methods of preventing PML in a subject having or at risk for having PML, comprising administering to the subject an effective amount of the pharmaceutical composition comprising the antisense ODNs described herein.

In preferred embodiments, the subject is an immunosuppressed or immunocompromised subject.

The invention preferably features treating a subject having or at risk of having PML. However, a number of diseases or disorders are suitable for treatment according to the methods of the invention. Examples include, but are not limited to neuroimmune disorders as well as Adenoma, Ageing, AIDS, Alopecia, Alzheimer's disease, Anemia, Arthritis, Asthma, Atherosclerosis, Cancer, Cardiac conditions or disease, Diabetes mellitus, Foodborne illness, Hemophilia A-E, Herpes, Huntington's disease, Hypertension, Headache, Influenza, lymphomas, Multiple Sclerosis, Myasthenia gravis, Neoplasm, Obesity, Osteoarthritis, Pancreatitis, Parkinson's disease, Pelvic inflammatory disease, Peritonitis, Periodontal disease, Rheumatoid arthritis, severe plaque psoriasis, Sarcoidosis, Sepsis, Sickle-cell disease, systemic lupus erythematosis, Teratoma, Ulcerative colitis, and Uveitis.

The methods of the invention further encompass diagnostics.

The methods may be practiced in an adjuvant setting. "Adjuvant setting" refers to a clinical setting in which, for example, an individual has had a history of PML, or the subject is immunocompromised, and therefore these individuals are considered at risk of development of the PML. Treatment or administration in the "adjuvant setting" refers to a subsequent mode of treatment. The degree of risk (i.e., when an individual in the adjuvant setting is considered as "high risk" or "low risk") depends upon several factors, most usually the extent of disease when first treated. The methods provided herein may also be practiced in a neoadjuvant setting, i.e., the method may be carried out before the primary/definitive therapy. Thus, in some embodiments, the individual has previously been treated. In other embodiments, the individual has not previously been treated. In some embodiments, the treatment is a first line therapy.

Dosing

The pharmaceutical compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Progressive multifocal leukoencephalopathy (PML) is a relatively rare, often fatal CNS demyelinating disease, which results from polyomavirus JC (JCV) under immunosuppressive conditions. Presently, there is clinically no cure. Developing chemical drugs against viral entry and replication have demonstrated severe side-effects, which have limited their application. Interference RNA technique has been recently introduced to suppressive protein products and replication of JCV, but has questionable nuclear stability. In the examples described herein, phosphorothioate antisense DNAs were examined targeting distinctive regions of JCV VP1, small t-Ag and large T-Ag in cultured human progenitor-derived astrocytes (PDAs) either transiently transfected with JCV genome-containing plasmid pM1TC or freshly infected with Mad 4 stain of JCV. A co-transfection of pM1TC with antisense DNA JCV#3 or JCV#14 targeting the domain of T-Ag immunocytochemically reduced T-Ag+ subpopulation by 56% and 76%, respectively. A post-infection treatment with JCV#3 and JCV#14 following JCV infection separately decreased T-Ag+ subpopulation by 71% and 62%. Similarly, VP1 antisense DNA VP1-3 targeting the area away from both N- and C-terminals of VP1 maximally decreased VP1+ subpopulation by 44%. In addition, T-Ag antisense JCV#3 significantly suppressed JCV replication. In situ hybridization revealed that JCV#3 at tolerant range suppressed JCV+ subpopulation by 88% in PDA culture that was freshly infected with JCV and by 78% in a persistently-infected culture of the SVG-derivative line 10B1 (Ferenczy, et al. 2013) (cell line 10B1-JCV also called 10B1-Mad4 because it is infected with the JCV Mad-4 strain). Due to the nature of phosphorothioate antisense DNA in stability, solubility and excellent bioactivities against protein products and replication of JCV, these studies demonstrate that antisense DNAs targeting specific regions of JCV may provide a novel approach for PML therapy.

Example 1

Blocking T-Ag Products with Antisense DNAs Reduces the T-Ag Positive Population

Figure 3B:
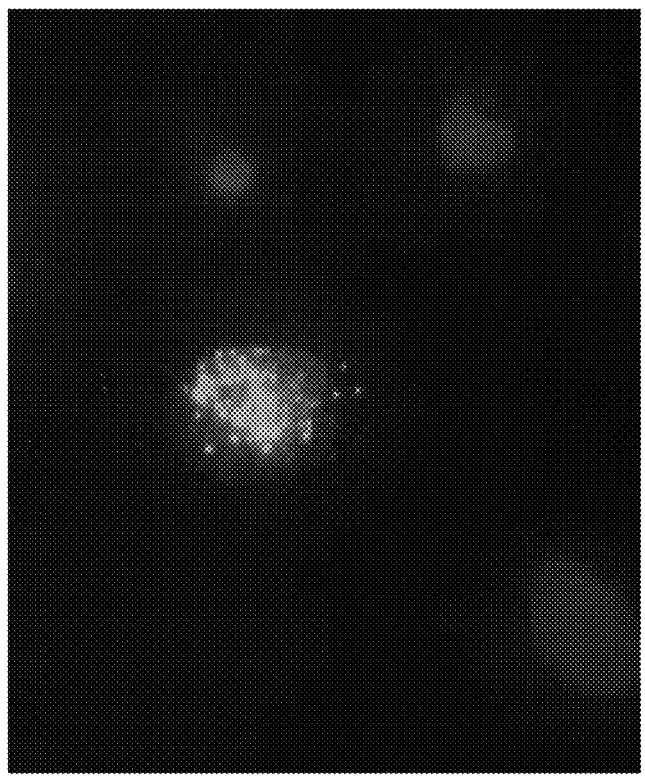
FIG. 3 shows intracellular distribution of T-Ag and percentage of T-Ag$^+$ cells following pM1TC transfection. PDA cells were transfected with 4.5 ug/well pM1TC by using lipofectamine 2000. T-Ag expression (green) in pM1TC-transfected cells were determined with anti-T-Ag antibody by immunocytochemistry. The specimens were co-stained with DAPI (blue). (A) The pM1TC-transfected culture after 5 days was photographed under DIC and (B) fluorescence. T-Ag signal was predominantly located in nucleus of astrocyte. (C) pM1TC-transfected culture after 9 days was stained without primary antibody to serve as a staining control, and T-Ag cannot be detected in absence of the primary antibody. (D) T-Ag signal was detectable in numerous cells when specimen was stained with anti-T-Ag antibody. (E) T-Ag$^+$ cells were shown as a percentage of DAPI-stained total cells and expressed as mean±SD. n=2; ***: $p<0.001$ by T-test.
Figure 3A:
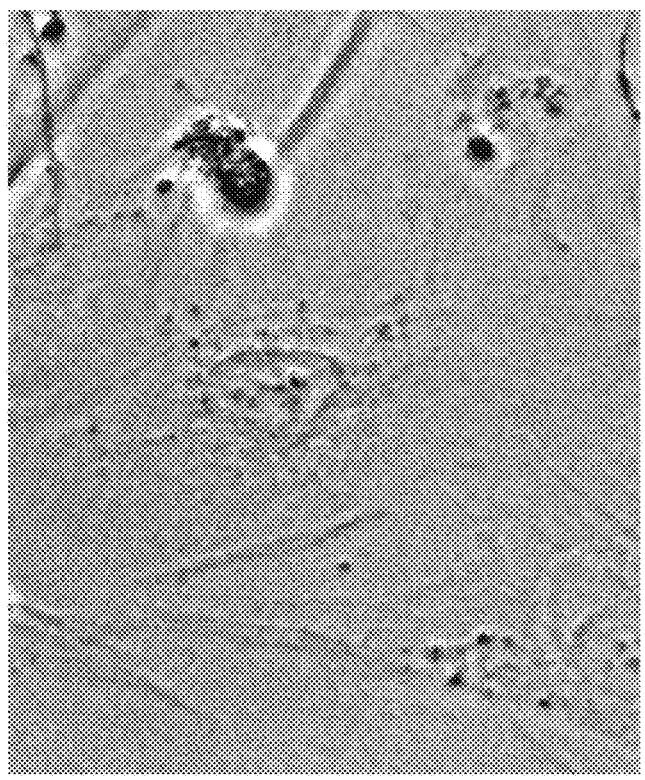
Figure 3D:
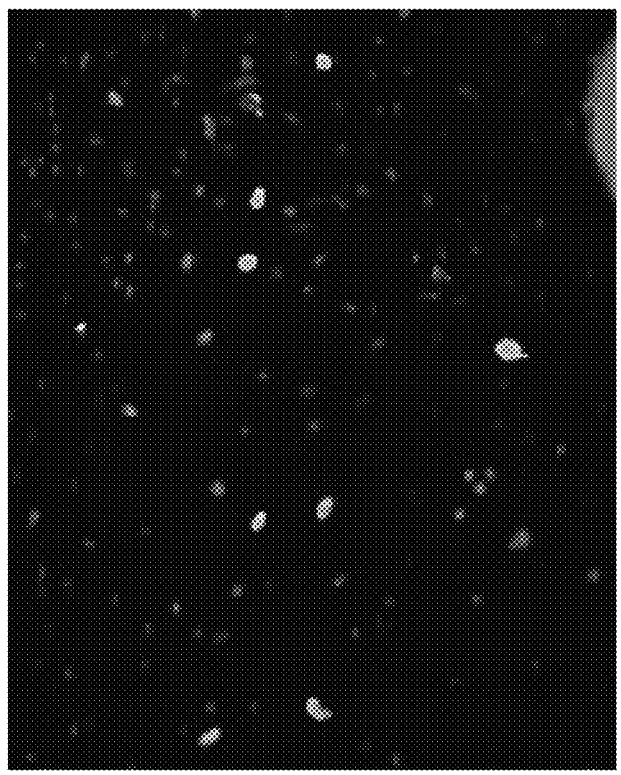
Figure 3C:
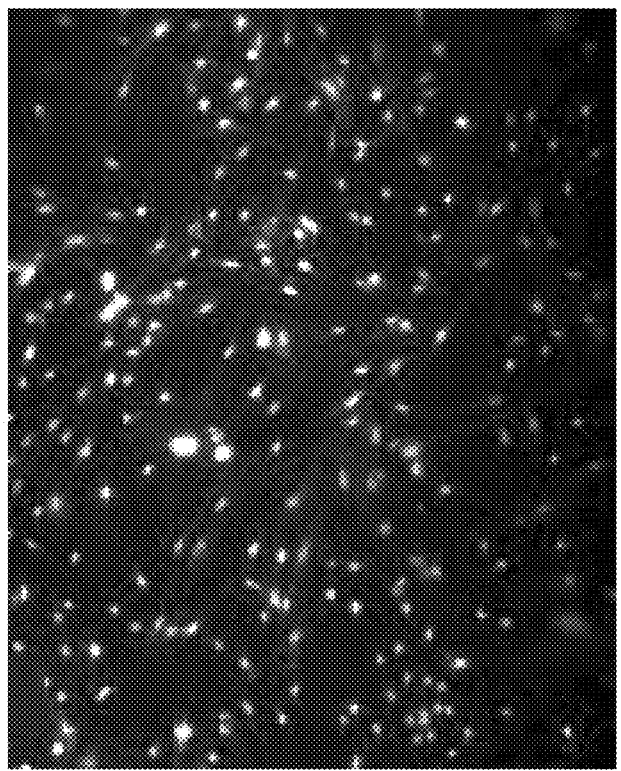
Figure 3E:
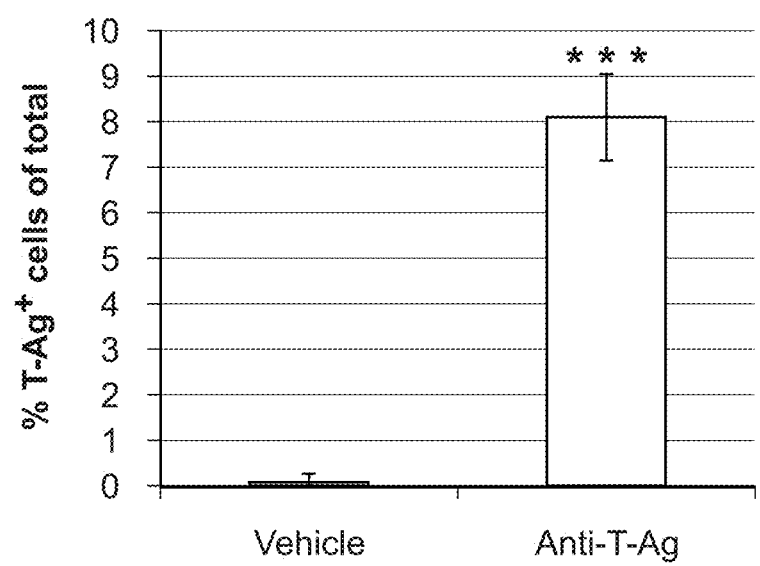
Figure 4A:
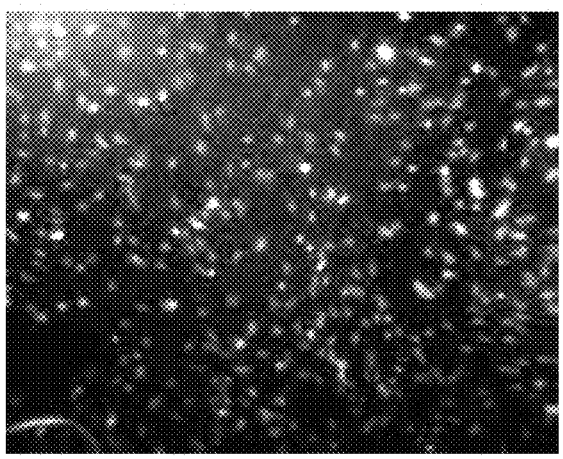
FIG. 4 shows suppression of T-Ag positive population of pM1TC-transfected PDA cells with JCV$^{\#}$3 and JCV$^{\#}$14, but not JCV$^{\#}$8 and JCV$^{\#}$13. (A) PDA cells were transfected with only vehicle (left image), with 4.5 ug/well pM1TC (center image) or with both 4.5 ug/well pM1TC and 5 ug/well JCV$^{\#}$3 (right image), and cultured for another 5 days. Cells were double stained with anti-JCV T-Ag antibody (green) and DAPI (blue). (B-E) PDA cells were co-transfected with 4.5 ug/well pM1TC and 0, 0.03, 0.06, 0.13, 0.25 and 0.5 ug/well of JCV$^{\#}$3, JCV$^{\#}$14, JCV$^{\#}$8 or JCV$^{\#}$13, and cultured for another 5 days. Percentage of T-Ag$^+$ cells in relationship to the number total cells was immunocytochemically determined by double staining with both DAPI and anti-JCV T-Ag antibody. Data for JCV$^{\#}$3 and JCV$^{\#}$13 are representative of three independent experiments while data for JCV$^{\#}$14 and JCV$^{\#}$8 are representative of two independent experiments. The data were expressed as mean percentages of the pM1TC-transfected, non-antisense-control value±standard deviations (SD). Statistical analysis was carried out with ANOVA assay followed by Tukey HSD Test at significance level of 0.01. ** $P<0.01$ comparing with control of pM1TC-transfection alone in efficacy evaluation; $^{\#}$ $P<0.05$ and $^{\#\#}$ $P<0.01$ comparing with control of pM1TC-transfection alone in cytotoxic evaluation.
Figure 4A:
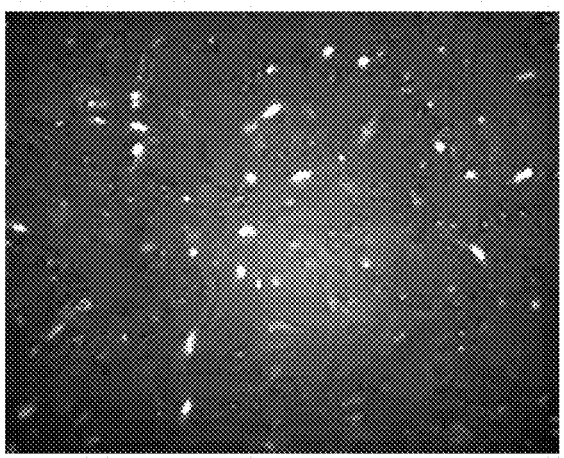
Figure 4A:
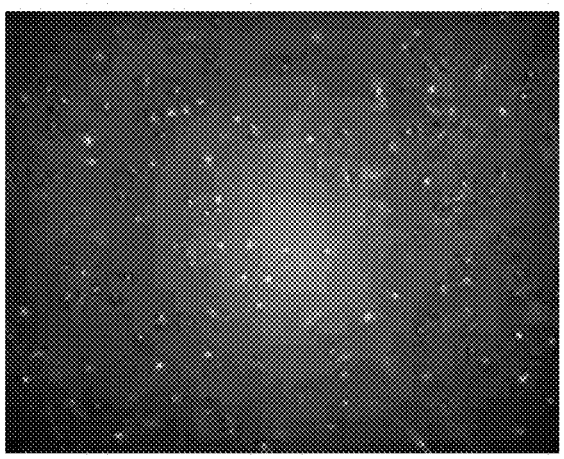
Figure 4B:
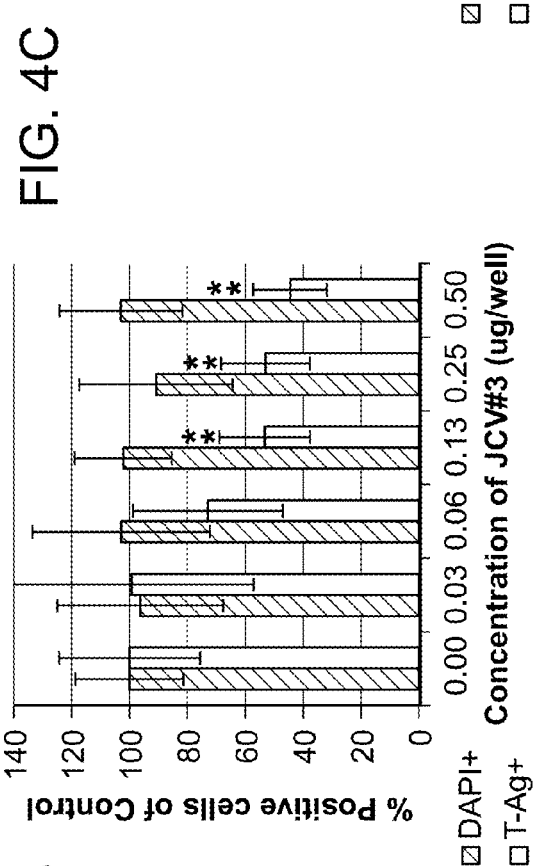
Figure 4D:
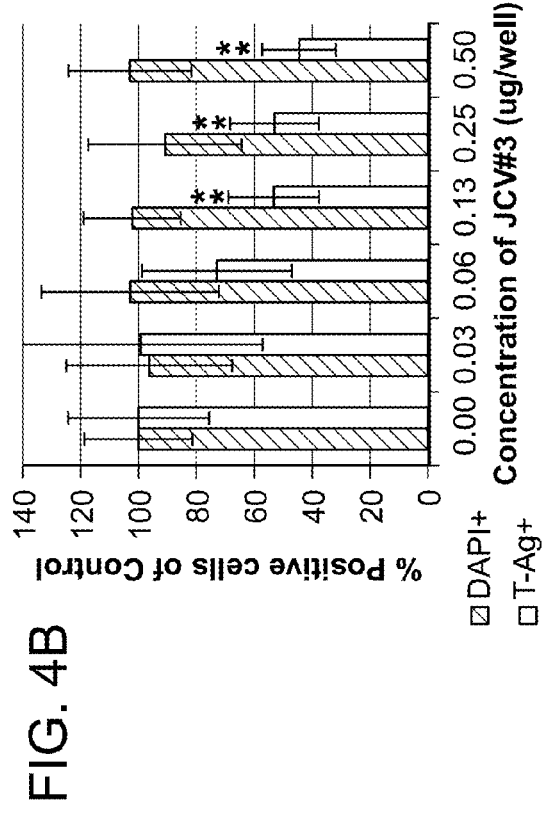
Figure 4C:
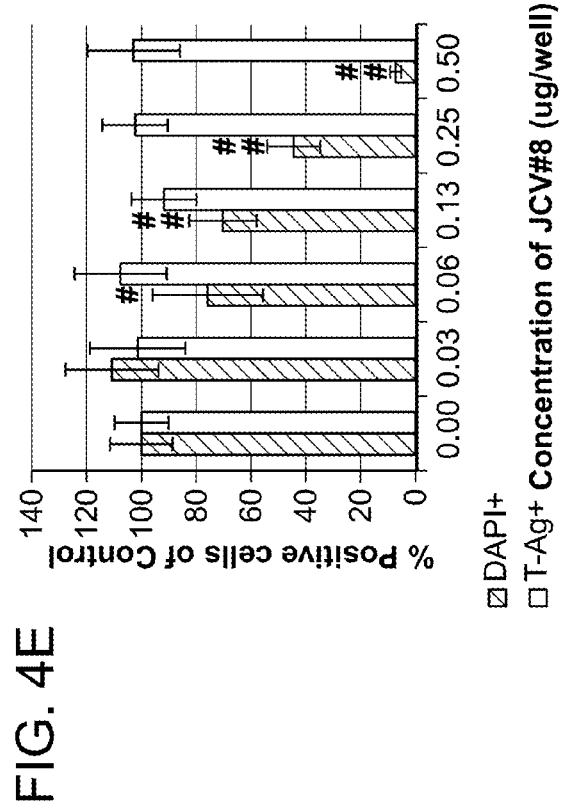
Figure 4E:
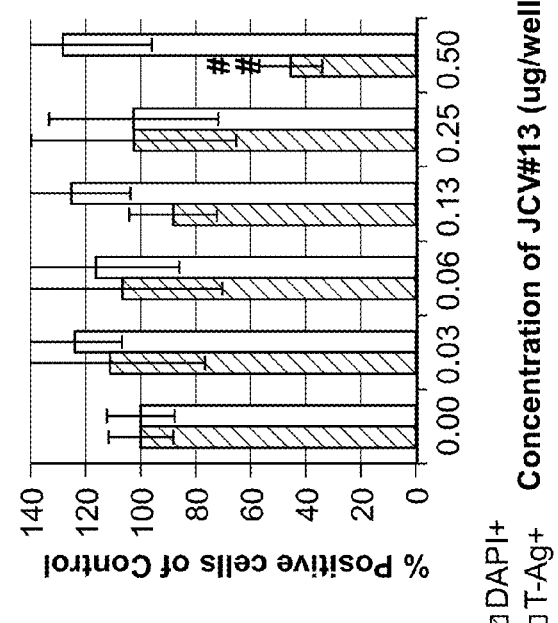

The effect of antisense DNAs were initially examined in a transient expression system of T-Ag protein where PDAs were transfected with JCV genome-containing plasmid pM1TC. To determine the transfection efficiency and distribution of this plasmid, the PDA cells were seeded on glass coverslips, transfected with 4.5 ug/well pM1TC, and co-stained by 5 and 9 days with both DAPI and AF-488 conjugated antibody against SV40 T-Ag, which cross-reacts with JCV T-Ag. Under differential interference contrast (DIC, FIG. 3A), PDA showed as large, flat cell with olivary-shaped nucleus which was stained blue with DAPI under fluorescence (FIG. 3B), allowing the determination of the total cell number per coverslip. The cells receiving pM1TC were stained green in the cell nucleus with the antibody against SV40 T-antigen (FIG. 3B). By 5 days following transfection, T-Ag staining presented as green granules in the nucleus, which were visible under higher magnification (FIG. 3B). By 9 days following transfection, T-Ag signal became stronger (FIG. 3D), which cannot be detected when a specimen was stained in absence of the primary antibody (FIG. 3C). Quantitatively, the T-Ag$^+$ cells were 8.1% of total cell in pM1TC-transfected culture, while it was negative in carrier control (no pM1TC) of the immunostaining (FIG. 3E).

In a first set of experiments, the effects of antisense DNAs (JCV#3 and JCV#14) against large T-Ag on the numbers of T-Ag+ were originally examined at concentrations of 0, 0.03, 0.06, 0.125, 0.25 and 0.5 ug/well in pM1TC (4.5 ug/well)-transfected PDA cultures, while antisense DNAs (JCV#8 and JCV#14) against VP2/3 were used as sequence-specific controls. 5 days following transfection, the cells were immunostained with antibodies against SV40 T-Ag, and co-stained with DAPI to measure total cell number, determine cell toxicity, and for normalization.

JCV#3 and JCV#14 dose-dependently suppressed the number of T-Ag+ cells (FIG. 4). Maximal inhibition was at 0.5 ug/well, where T-Ag+ cells decreased by 56% and 76%, respectively. In contrast, JCV#8 and JCV#13 did not affect T-Ag+ cell number in any tested concentration.

Regarding cell toxicity, JCV#8 dose-dependently elicited cell death with a starting concentration of 0.06 ug/well. JCV#13 induced cell death only at 0.5 ug/well. Reduction of T-Ag+ cell percentage by antisense DNA at a concentration of 0.25 ug/well is summarized in Table 1, below. Data for JCV#3 and JCV#13 were averaged from triplicate experiments, and those for JCV#14 and JCV#8 were averaged from duplicate experiments.

TABLE 1

% Reduction of T-Ag+ Positive Cells by Antisense DNAs

| Antisense DNAs | Target Region | % T-Ag decrease |
|---|---|---|
| JCV#3 | T | 47 |
| JCV#14 | T | 59 |
| JCV#8 | VP2/3 | 0 |
| JCV#13 | VP2/3 | 0 |

Antisense DNAs JCV$^\#$3 and JCV$^\#$14 designed against T-Ag were examined in pM1TC-transfected PDA cells to determine their effects on cell population expressing large T-Ag protein, while using JCV$^\#$8 and JCV$^\#$13 designed against products of VP2/3 coding regions as controls (FIG. 4). In the culture without pM1TC transfection, the full population of PDA culture showed blue stained nuclei (FIG. 4A, left panel). When cells were transfected with 4.5 ug/well pM1TC, the pM1TC-receiving cells showed nuclei in green (FIG. 4A, center panel). A co-transfection of pM1TC with 5 ug/well JCV$^\#$3 greatly suppressed the green T-Ag signal in the nuclei (FIG. 4A, right panel). In a study of increasing concentrations of antisense DNA, JCV$^\#$3 or JCV$^\#$14 at a concentration range from 0.03 ug/well to 0.5 ug/well did not elicit any cytotoxicity by 5 days following co-transfection with pM1TC and an antisense DNA (FIGS. 4B and 4C). JCV$^\#$13 at concentrations equal to or less than 0.25 ug/well did not result in cytotoxicity, but induced cell death (54%) at 0.5 ug/well (FIG. 4D). In contrast, JCV$^\#$8 at the concentrations above 0.06 ug/well elicited significant cell loss with maximal cell reduction by 93% (FIG. 4E). JCV$^\#$3 or JCV$^\#$14 dose-dependently reduced T-Ag$^+$ cell population (FIGS. 4B and 4C). By comparing with pM1TC (no antisense)-transfected group, the maximal effect was achieved when cells were transfected with 0.5 ug/well JCV$^\#$3 or JCV$^\#$14, reducing T-Ag positive cells by 56% and 76% respectively. In contrast, JCV$^\#$13 or JCV$^\#$8 did not change the population of the T-Ag positive cells in number (FIGS. 4D and 4E, respectively).

Figure 5C:
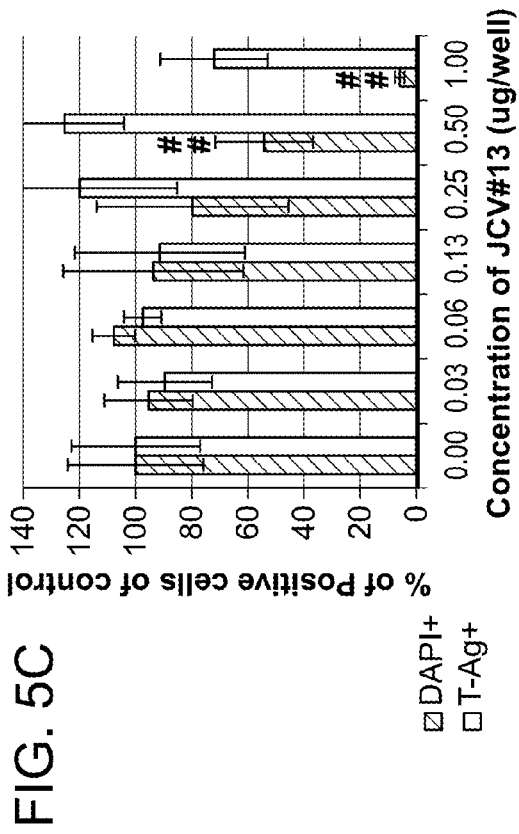
FIG. 5 shows suppression of T-Ag by JVC#3, but not JCV#13, Scramble 1 control, and Scramble 3 control in Mad 4 JCV-infected PDA cells. (A) PDA cells were infected with 200 HAu per 1 million cells. The next day they were transfected with different concentrations of JCV$^{\#}$3 and JCV$^{\#}$13 and then cultured for 15 days. The cells were then double stained with anti-JCV T-Ag antibody (green bar) and DAPI (blue bar). (B-E) JCV-infected PDA cells were transfected with JCV$^{\#}$3, JCV$^{\#}$13, Scramble 1 (Scram 1) or Scramble 3 (Scram 3), stained with both DAPI and anti-JCV T-Ag antibody, and quantitatively analyzed. Data for JCV$^{\#}$3 and JCV$^{\#}$13 are representative of three or four independent experiments, respectively. The data were expressed as mean percentages of the JCV-infected, non-antisense-control value±standard deviations (SD). Statistical analysis was carried out with ANOVA assay followed by Tukey HSD Test at significant level of 0.01. ** $P<0.01$ comparing with control of JCV-infected alone in efficacy evaluation; $^{\#\#}$ $P<0.01$ comparing with control of JCV-infected alone in cytotoxic evaluation.
Figure 5B:
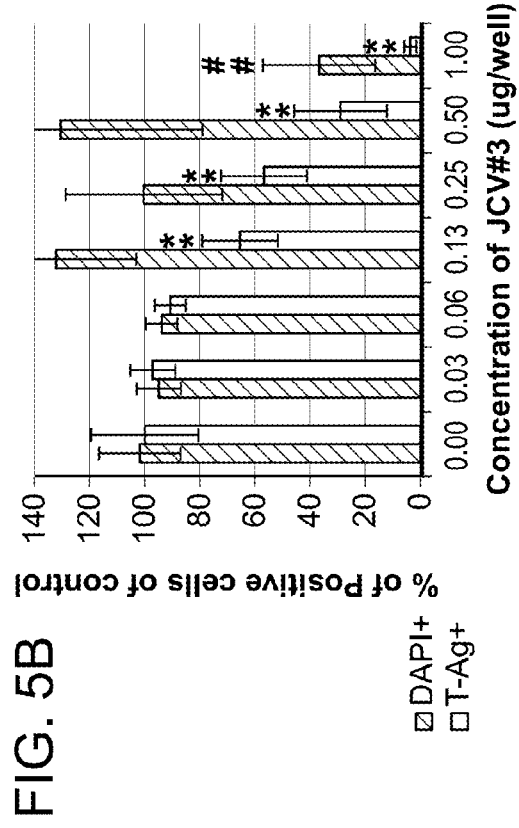
Figure 5E:
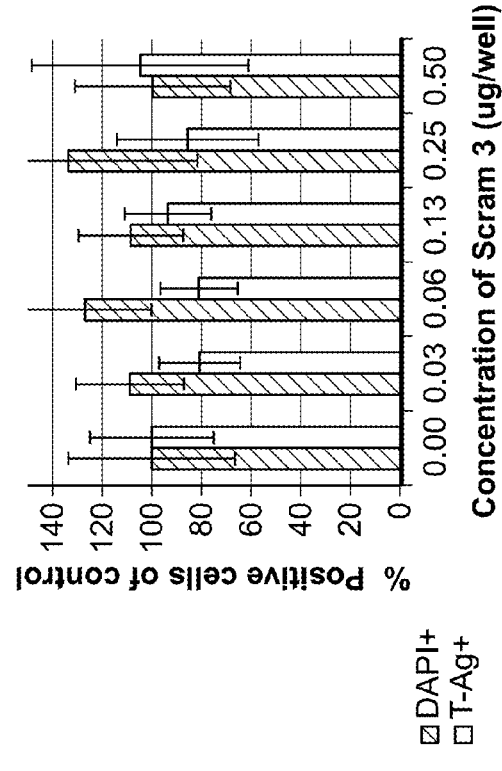
Figure 5D:

To understand if these antisense DNAs affect the number of T-Ag$^+$ PDA cells that contains full JCV virion, the PDA cells were infected with Mad 4 strain of JCV one day before transfection with 0, 0.03, 0.06, 0.125, 0.25, 0.5 and 1.0 ug/well of JCV$^\#$3 or JCV$^\#$13. 15 days following transfection, the cytotoxicity and efficacy of above antisense DNAs were separately evaluated with comparison of DAPI$^+$ and T-Ag$^+$ cells in a group with these in JCV-infection alone group (FIG. 5A). JCV$^\#$3 dose-dependently reduced T-Ag$^+$ cell subpopulation (green) while the whole cell population remained unchanged (blue). In contrast, JCV$^\#$13 at 0.5 ug/well elicited cytotoxicity, and a decrease in both viable cells and the T-Ag$^+$ subpopulation. In the rest of the conditions, JCV$^\#$13 did not reduce T-Ag$^+$ subpopulation. Quantitatively (FIG. 5B), JCV$^\#$3 dose-dependently reduced number of T-Ag$^+$ cells, with maximal suppression by 71% under non-toxic concentrations (<0.5 ug/well). Although at 1 ug/well JCV$^\#$3 nearly completely (96%) removed T-Ag$^+$ cells from culture, it elicited cell death by 63% under this condition. In comparison, JCV$^\#$13 at and above 0.5 ug/ul elicited cytotoxicity shown by reduced number of DAPI$^+$ cells, although it reduced subpopulation of T-Ag$^+$ cells as well (FIG. 5C). After normalization against the total cell number, JCV$^\#$13 showed no suppressive effect on T-Ag$^+$ cells. PDA cells were infected with Mad 4 strain of JCV one day before transfection with 0, 0.03, 0.06, 0.125, 0.25 and 0.5 ug/well of Scramble 1 or Scramble 3. 15 days following transfection, Scramble 3 in tested concentration range did not elicit any cytotoxicity and T-Ag suppression (FIG. 5E). In contrast, Scramble 1 at 0.25 and 5 ug/well caused cell death, reducing 49% of total cells (FIG. 5D). Within the non-cytotoxic concentration, it did not reduce T-Ag⁺ subpopulation. Due to the cytotoxicity of Scramble 1, it was eliminated from further studies, while Scramble 3 was further used as a non-specific control.

Example 2

The Effects of Antisense DNAs Against T-Ag and VP1 are Target Sequence Dependent The sequence-dependent specificity of T-Ag suppression by JCV#3 and JCV#13 were further clarified in pM1TC-transfected PDA cells. Due to the cytotoxicity in the previous experiments using pM1TC co-transfection model, JCV#8 was eliminated from this (JCV-infected) and further studies. Instead, deoxynucleotides with random-distributed order, including Scramble 1 and Scramble 3, were included as additional sequence negative controls (FIGS. 5D and 5E).

In another set of experiments, the effects of antisense DNAs against large T-Ag (JCV#3 and JCV#14), against large T-Ag, small T-Ag, and the minor T-Ag splice variants (LgT-1, and LgT-2), against VP2/3 (JCV#8 and JCV#14), and against VP1 (VP1-2, VP1-3 and VP1-4) on the numbers of T-Ag+, VP1+ and JCV+ cells were examined Concentrations used were 0, 0.03, 0.06, 0.125, 0.25, 0.5 and 1 ug/well, one day following JCV infection of PDA cells at 200 HAu/million cells. The scramble 1 and scramble 3 antisense DNAs were included as sequence-specific control in the same range of concentrations as above. 15 days following transfection, the cells were separately immunostained with antibodies against T-Ag and VP1 or intracellular JCV was detected by in situ hybridization.

Figure 6A:
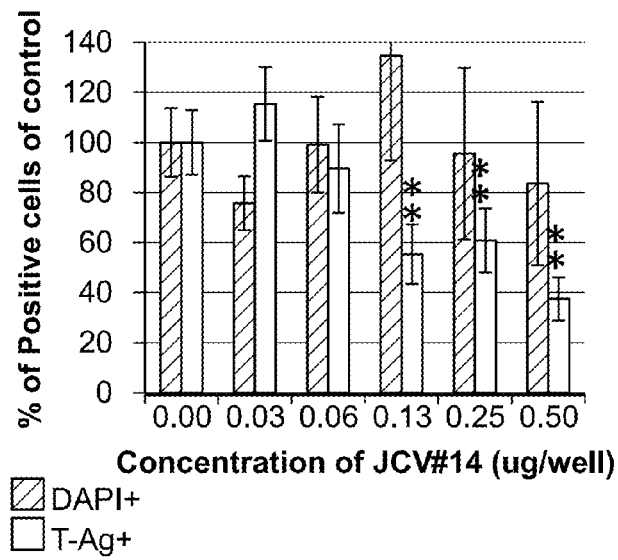
FIG. 6 shows suppression of T-Ag by JCV#14, LgT-1, or LgT-2 in Mad 4 JCV-infected PDA cells. PDA cells were infected with 200 HAu per 1 million cells, then transfected the next day with 0, 0.03, 0.06, 0.13, 0.25 and 0.5 ug/well of JCV$^{\#}$14 (A), LgT-1(B) and LgT-2 (C), and cultured for 15 days. At the end, the cells were double stained with anti-JCV T-Ag antibody (green bar) and DAPI (blue bar). Data for JCV$^{\#}$14 are representative of two experiments. The data were expressed as mean percentages of the JCV-infected, non-antisense-control value±standard deviations (SD) from 5 randomly chosen photo areas. Statistical analysis was carried out with ANOVA assay followed by Tukey HSD Test at significant level of 0.01. ** P<0.01 comparing with control of JCV-infected alone in efficacy evaluation; ## P<0.01 comparing with control of JCV-infected alone in cytotoxic evaluation.
Figure 6B:
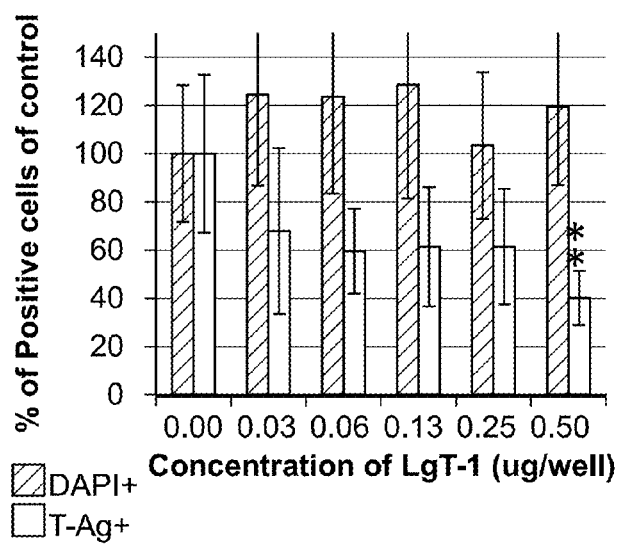
Figure 6C:
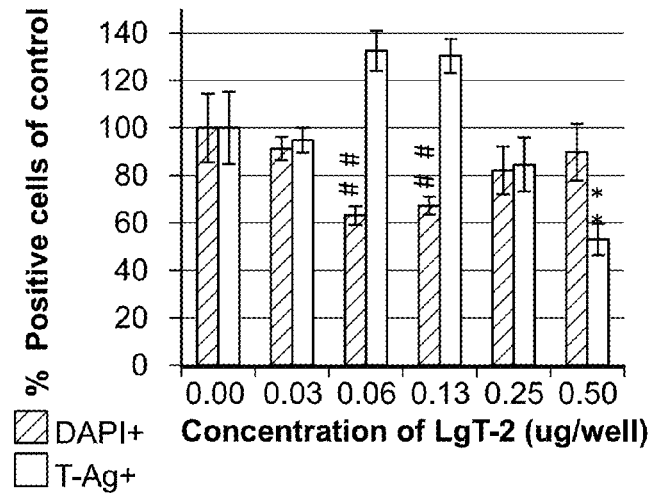

JCV#14 dose-dependently suppressed the number of T-Ag+ cells (FIG. 6A). JCV#14 started suppressing T-Ag⁺ subpopulation by 45% at a concentration of 0.125 ug/well. JCV#14 did not elicit any cytotoxicity in tested concentration range. LgT-1 and LgT-2 also dose-dependently suppressed the number of T-Ag+ cells, but had less effect than JCV#3 and JCV#14 (FIGS. 6B and C). LgT-1 in tested concentration range did not elicit toxicity to JCV-infected PDA cells (FIG. 6B). It only reduced T-Ag⁺ subpopulation at a concentration of 0.5 ug/well. Similarly, LgT-2 only suppressed T-Ag⁺ subpopulation at 0.5 ug/well (FIG. 6C).

Figure 7A:
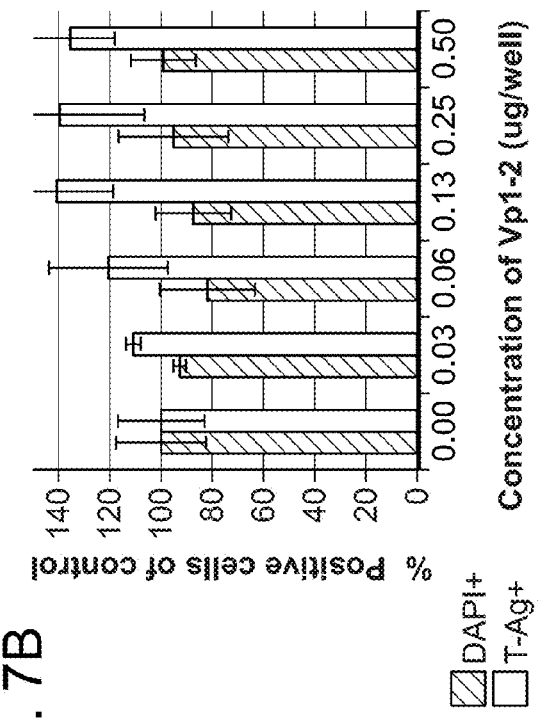
FIG. 7 shows suppression of VP1, but not T-Ag, by VP1-2, VP1-3, and VP1-4 antisense oligonucleotides in Mad 4 JCV-infected PDA cells. PDA cells were infected with 200 HAu per 1 million cells, then transfected the next day with 0, 0.03, 0.06, 0.13, 0.25 and 0.5 ug/well of VP1-2 (A and B), VP1-3 (C and D) and VP1-4 (E and F), and cultured for 15 more days. At the end, the cells were double stained with DAPI (blue bar) and anti-JCV VP-1 (Orange bar in A, C and E) or anti-JCV T-Ag (green bar in B, D and F) antibody. Data are representative of two independent experiments. Statistical analysis was carried out with ANOVA assay followed by Tukey HSD Test at significant level of 0.01. * P<0.05 and ** P<0.01 comparing with control of JCV-infected alone in efficacy evaluation; # P<0.05 and ## P<0.01 comparing with control of JCV-infected alone in cytotoxic evaluation.
Figure 7B:
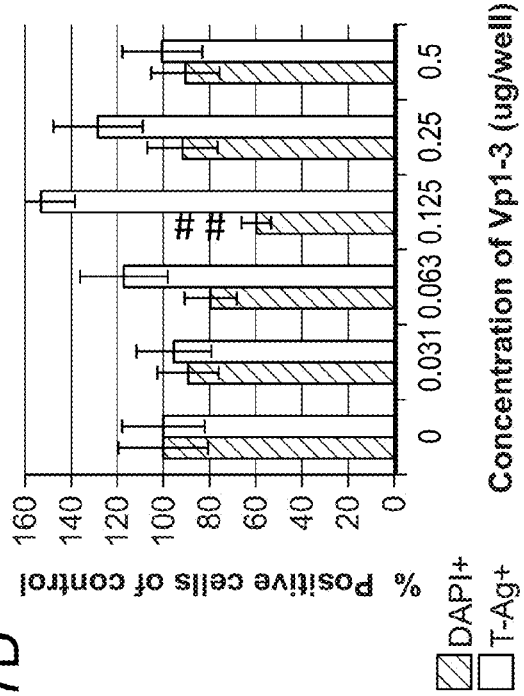
Figure 7C:
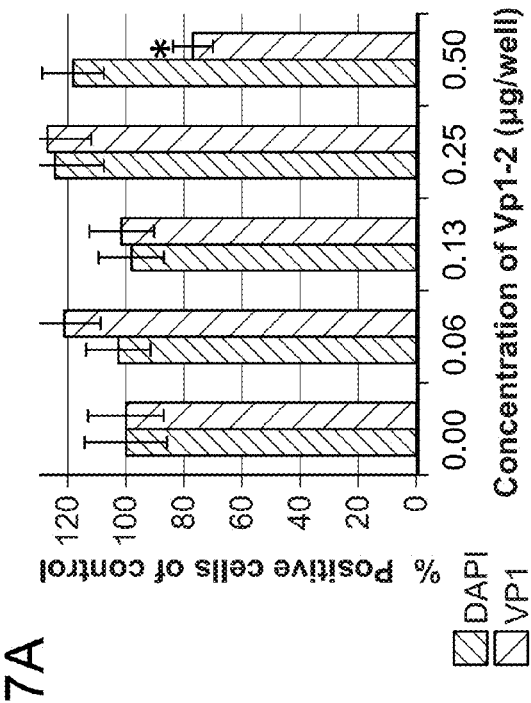
Figure 7D:
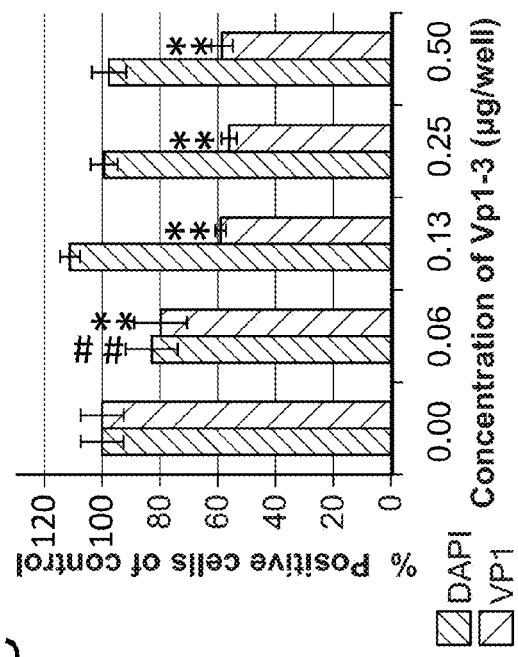
Figure 7F:
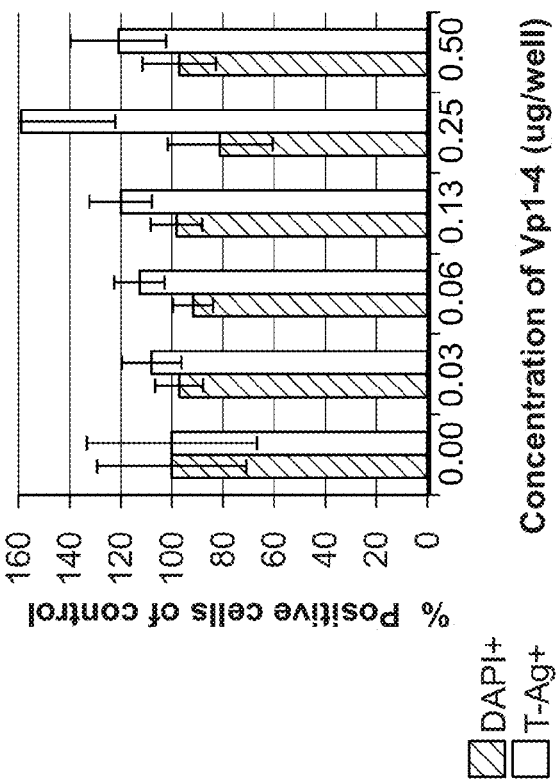
Figure 7E:
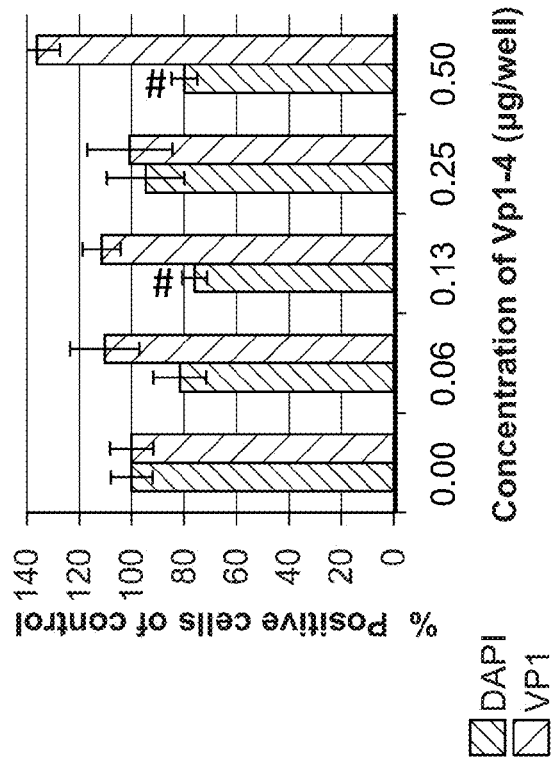

The effect of antisense DNAs against JCV VP1 on VP1+ cell number was examined VP1-2 decreased VP1+ cells only at the highest test concentration (0.5 ug/well in this case) (FIG. 7A), while VP1-4 had no effect on VP1+ cell number (FIG. 7E). VP1-3 dose-dependently decreased the percentage of VP1+ cells (FIG. 7C). Taking Scramble 3 as experimental control, the best antisense DNAs JCV#3 and VP1-3 (at 0.25 ug/well for each) with different target regions is summarized in Table 2, below. Concentration the antisense DNA was 0.25 ug/well, data from T-Ag were averaged from four independent experiments, and data from VP1 was from one experiment.

TABLE 2

| % Reduction of Positive Cells by Antisense DNAs | | | | |
|---|---|---|---|---|
| Antisense DNAs | Target Region | % T-Ag decrease | % VP1 decrease | % JCV decrease |
| JCV#3 | T | 71 | N/A | 60 |
| VP1-3 | VP1 | 0 | 44 | N/A |
| Scramble 3 | N/A | 0 | N/A | N/A |

Example 3

Vp1-3 Reduced VP-1, but not T-Ag, Population

In JCV-infected PDA culture, the antisense DNAs against VP-1 RNA were also examined to determine their effect on VP-1⁺ subpopulation. VP1-2, VP1-3 and VP1-4 did not consistently reduce DAM⁺ cell numbers across various concentrations (FIG. 7).

At 0.5 ug/well VP1-2 suppressed VP-1⁺ cells by 23% (FIG. 7A). Antisense VP1-2 neither elicited cytotoxicity nor affected T-Ag⁺ subpopulation (FIG. 7B). Antisense VP1-3 dose-dependently reduced VP-1⁺ subpopulation and achieved 41% suppression at a concentration as low as 0.13 ug/well (FIG. 7C). Antisense VP1-3 did not elicit any changes of T-Ag⁺ subpopulation at any concentration (FIG. 7D). Antisense VP1-4 showed no effect on VP-1⁺ subpopulation (FIG. 7E). Similarly, antisense VP1-4 did not reduce the T-Ag⁺ subpopulation (FIG. 7F).

Example 4

Blocking T-Ag Products with Antisense DNAs Decreased the Percentage of JCV-Genome Positive Cells The effect of T-Ag antisense JCV#3 on the JCV genome positive (JCV⁺) subpopulation was examined to understand if blocking T-Ag translation could affect JCV genome replication. Antisense JCV#13 against VP2/3 region was used as an experimental control. JCV-infected PDA cells were transfected with antisense DNA. 15 days following transfection the cultures were examined by in situ hybridization and counter-stained with hematoxilyn to determine JCV⁺ subpopulation and total cell number. The nuclei of JCV⁺ cells stained dark brown under DIC (FIG. 8A, top left panel). JCV-infected cultures were also hybridized with nonspecific DNA probe (calf thymus DNA) as a control. No dark brown-stained nuclei were found (FIG. 8A, bottom left panel). JCV#3 transfection did not affect cell density (hemotoxylin-stained cells) at and below 0.5 ug/well, and reduced total cell number at 1 ug/well. At low-cytotoxicity concentrations, JCV#3 gradually reduced cell subpopulation with dark-stained nuclei (FIG. 8A). JCV#3 dose-dependently decreased number of JCV-containing cells with a maximal non-cytotoxic inhibition of 88% at 0.5 ug/ul (FIG. 8B). Although JCV#3 at 1 ug/well nearly completely remove JCV-containing cells from culture, it caused 86% cell death under this condition. In contrast, JCV#13 left cell density unchanged at and below 0.25 ug/well. Within non-cytotoxic concentrations, JCV#13 did not decrease in situ-stained subpopulation (FIG. 8A). JCV#13 did not change JCV⁺ subpopulation in the tolerated range of concentrations (FIG. 8C). JCV#13 at 0.5 and 1 ug/well reduced JCV-containing subpopulation by 55% and 90%, but caused a decrease in total cells by 71% and 89% respectively). Therefore, it was not considered a sequence-specific effect.

Figure 9A:
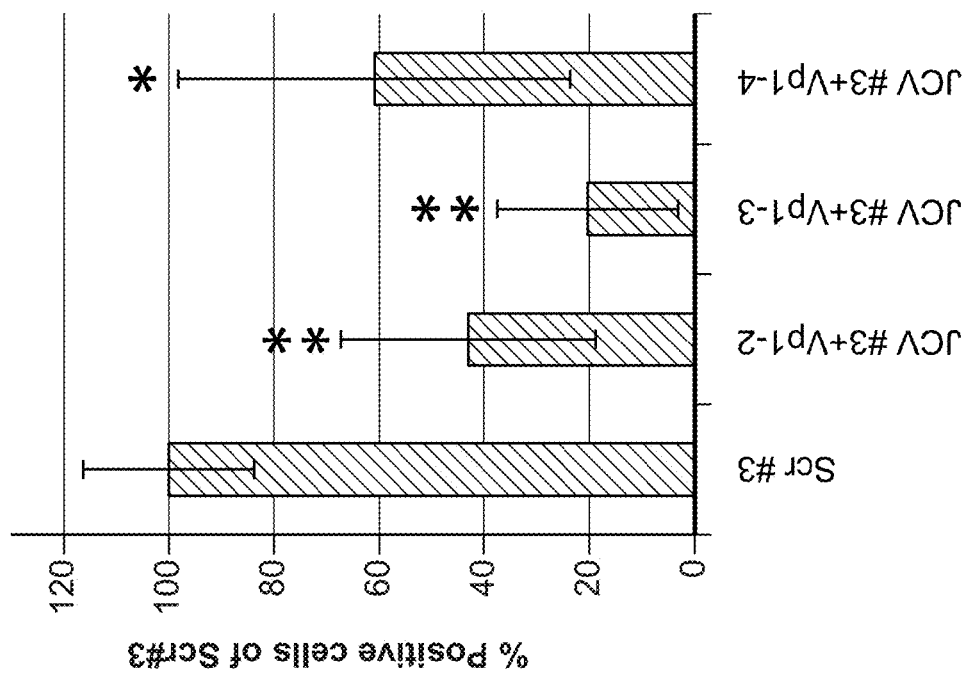
FIG. 9 shows the effect of a single and/or the combination of two different antisense DNAs on the JCV replication in 10B1 cell line persistently infected by JCV (10B1-JCV). (A) Persistently infected 10B1-JCV cells (Ferenczy, et al. 2013) were transfected with 0.25 ug/well of Scramble 3 control ($Scr^{\#}3$), $JCV^{\#}3$, VP1-2, VP1-3 and VP1-4 for 4 hours, and maintained in culture for 2 days. (B) 10B1-JCVcells were transfected with 0.25 ug/well Scr#3 or co-transfected with the combination of JCV#3 and VP1-2, or VP1-3 or VP1-4 for 4 hours, and maintained in culture for 2 more days. Data are representative of two independent experiments and are expressed as the mean percentages of the JCV-infected, non-antisense-control value±standard deviations (SD) of 5 randomly selected photo areas. Statistical analysis was carried out with ANOVA assay followed by Tukey HSD Test at significant level of 0.01. * P<0.05 and ** P<0.01 comparing with control of JCV-infected alone in efficacy evaluation.

The effect of JCV#3 on JCV replication was also examined in a persistently infected 10B1-JCV system where 10B1 cells were previously infected with JCV (Ferenczy et al. 2013). In one set of experiments, the effect of antisense DNA JCV#3, JCV#14, VP1-2, VP1-3 or VP1-4 at 0.25 ug/well on number of JCV+ cells was examined twice by in situ hybridization using the 10B1-JCV cell culture. JCV#3 significantly reduced JCV+ cell number by 78% (FIG. 9A). The mean value of JCV+ cell number in VP1-2 or VP1-3 group was less than that of Scramble 3 group but there was no significant statistical difference between Scramble 3 and VP1-2, VP1-3, or VP1-4 (FIG. 9A).

Example 5

Figure 9B:
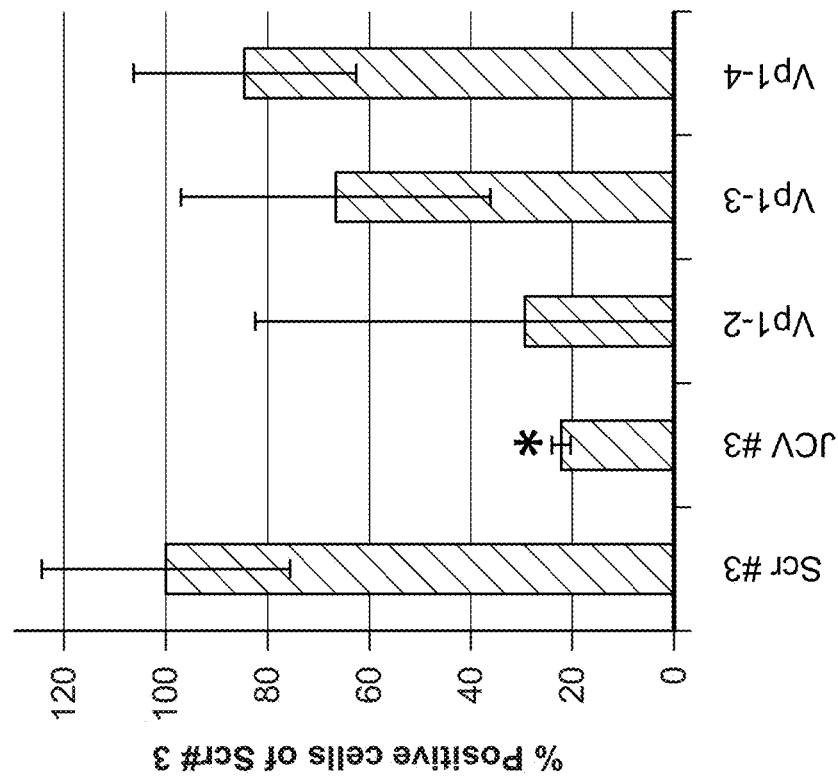

Combined Antisense DNAs Against Both T-Ag and VP-1 Did not Achieve a Synergistic Effect on JCV Replication Since antisense DNA JCV#3 reduced T-Ag$^+$ subpopulation and inhibited JCV genome replication and antisense VP1-3 reduced the VP1$^+$ subpopulation, co-transfection of JCV#3 with VP1-3, using Scramble 3 and co-transfection with VP1-2 or VP1-4 as experimental controls, was carried out. The 10B1-JCV cells were transfected with 0.25 ug/well of Scramble 3 or co-transfected with 0.25 ug/well of JCV#3 and 0.25 ug/well of VP1-2, VP1-3 or VP1-4. After 2 days cells were analyzed by in situ hybridization and counter-stained with hematoxilyn (FIG. 9B). The co-transfection with dual antisense DNAs targeting both T-Ag and VP-1 significantly reduced the JCV$^+$ subpopulation. Among them, a co-transfection of JCV#3 with VP1-3 achieved maximal effect by decreasing JCV$^+$ subpopulation by 80%, while co-transfection of JCV#3 with VP1-2 reduced JCV$^+$ subpopulation by 57%. However, co-transfection of antisense DNAs against T-Ag and VP1 did not decrease JCV+ cells by more than JCV#3 transfection alone (FIGS. 9A and B).

These results are similar to an early in vitro observation where using siRNA to abolish both JCV agnoprotein and VP1 did not gain an extra effect on hemagglutination activity than VP1 alone either (Orba et al., 2004). Additionally an effort using siRNAs for 15 days to abolish both JCV regulatory proteins T-Ag and agnoprotein did not achieve additional effect on viral replication than T-Ag siRNA alone either (Radhakrishnan et al., 2004). Because T-Ag is required for viral DNA replication and robust production of VP1 RNA, reduction of T-Ag may also drive reduction of viral DNA of VP1. In contrast, reduction of VP1 can affect JCV replication only when JCV virion exits the host cell and infects additional cells. Thus in vitro time frames may be too short to see a synergy between antisense DNAs.

In general, the studies described herein provide a target-oriented approach to suppressions of translation of JCV VP1 and T-Ag, and replication of JCV with antisense DNA. Compared to indirect inhibition of JCV replication with chemicals via suppression of host mitotic machinery, the target-oriented antisense technique directly influences JCV product and replication, and may achieve high ratio of beneficial/diverse effects in PML therapy. Upon finding the tolerable dose of these antisense DNAs in an animal model, further studies can be carried out to determine the dose necessary to suppress JCV replication in a human subject. Even though a synergic effect of T-Ag and VP1 antisense DNAs was not detected in present culture, it is still possible that there are such effects in vivo where JCV can be released from infected cells and efficiently spread to permissive cells in neighborhood. Antisense DNA against JCV represents a novel potential approach for PML therapy.

Example 6

Toxicity Studies

Figure 10:
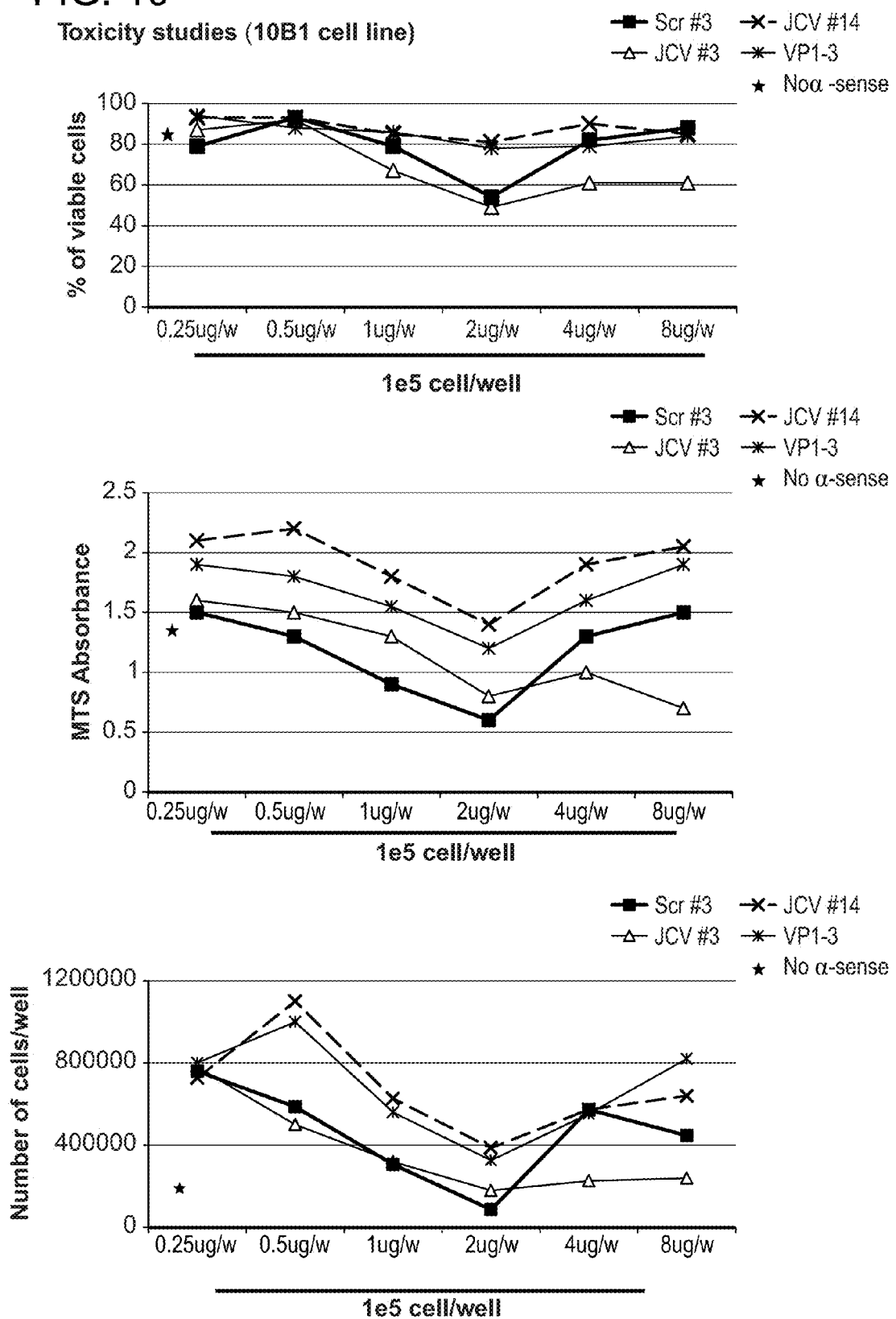
FIG. 10 shows results of toxicity studies performed using 10B1 cell line. To narrow down the optimal concentration and the number of antisense DNA to use in further experiments, a set of toxicity tests were employed. Three different antisense DNAs (JCV#3, JCV#14 and VP1-3) and a control DNA (scr #3) were used at increased concentration from 0.25 ug/well to 8 ug/well. Each well was seeded with 50,000 10B1 cells. JCV#14 and VP1-3 showed low level of toxicity at the lower concentrations of antisense DNA. Those experiments also showed that the scr #3 control DNA was toxic to the 10B1 cells. As a result of these data, further experiments were carried out only using JCV#14 and VP1-3 and a different control.
Figure 11:
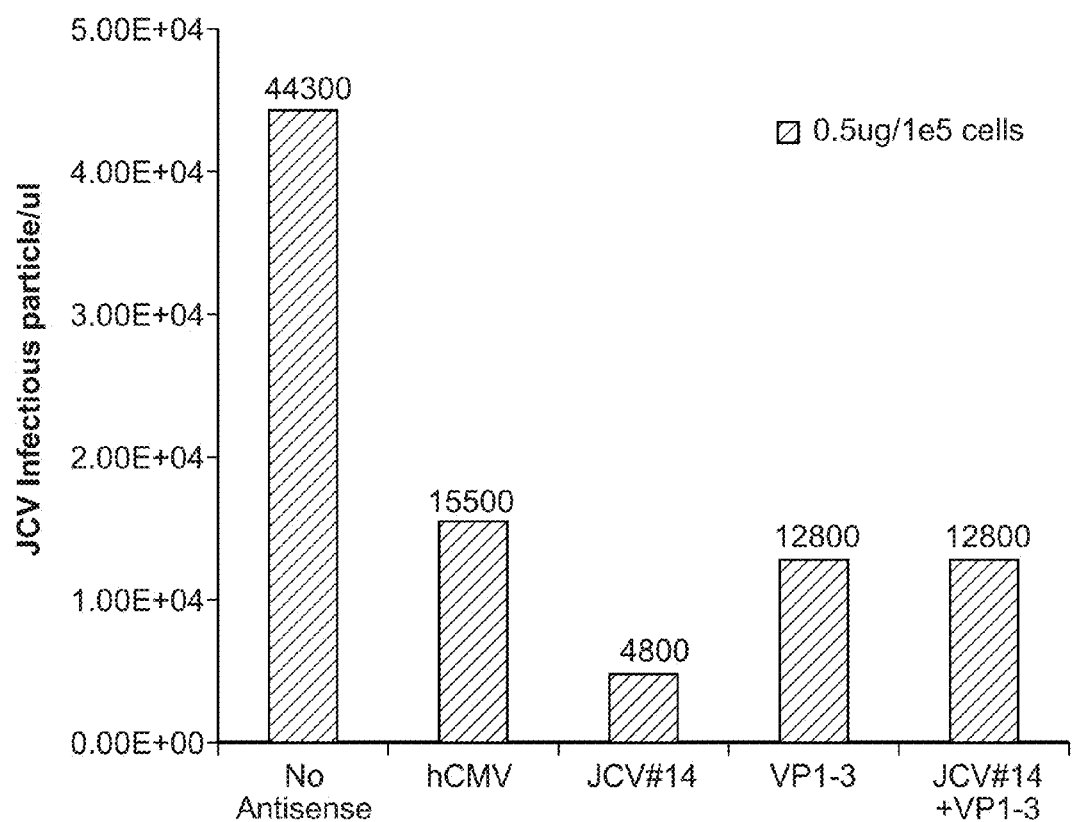
FIG. 11 shows the results of a hemaglutination (HA) assay performed three days post-transfection of 10B1-JCV with the new control DNA (hCMV), and JCV#14, VP1-3 and the combination of both. JCV#14 generated 3 fold decreases in JCV replication in comparison with the control, while data from VP1-3 and the combination of VP1-3 and JCV#14 were comparable to the control.

In this set of experiments, assessment of the cell toxicity of varying concentrations of antisense oligonucleotides in the 10B1 was carried out (FIG. 10). Three different antisense DNAs (JCV#3, JCV#14 and VP1-3) and a control DNA (scr #3) were used at increasing concentration from 0.25 ug/well to Bug/well. Each well was seeded with 50,000 10B1 cells. JCV#14 and VP1-3 showed low level of toxicity at the lower concentrations of antisense DNA. These experiments also showed that the scr #3 control DNA was toxic on the 10B1 cells. As a result of these data, further experiments were carried out using only JCV#14 and VP1-3 and a different control, hCMV. The hCMV antisense is an antisense to another human virus, cytomegalovirus, used as a negative control since its sequence is different from JCV. It has previously been used as an experimental control for antisense DNA experiments (Ma, et al. 2012).

Example 7

Hemaggluttinin Assays

Hemagglutinin (HA) is the measure of newly made virions harvested from cultures of 10B1 cells, persistently infected with JCV. There is no plaque assay for JCV. Consequently, virions are measured using their ability to hemagglutinate human type 0 erythrocytes in a limiting dilution experiment.

10B1-JCV cells were transfected with 0.5 ug/100,000 cells of antisense DNAs (control DNA (hCMV), and JCV#14, VP1-3 and the combination of both). 3 days post-transfection, a hemagglutination (HA) assay was performed. JCV#14, with added 2' O-methyl RNA bases on the 5' and 3' ends of the DNA. generated 3 fold decreases in JCV replication in comparison with the control, while HA from VP1-3 and the combination of VP1-3 and JCV#14 were comparable to the control.

Figure 12:
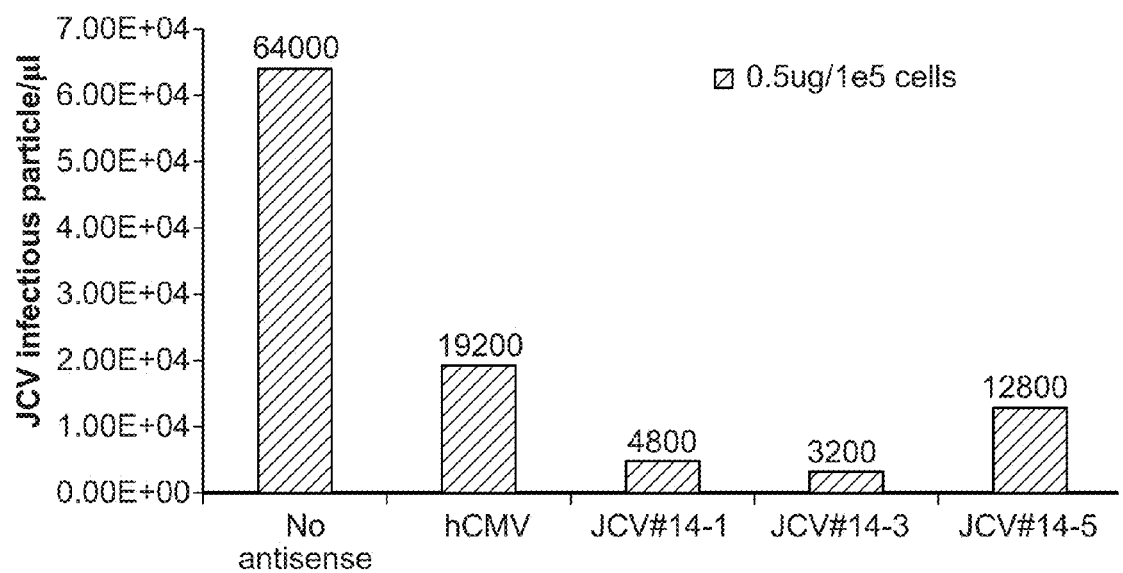
FIG. 12 shows the results of a hemaglutination (HA) assay performed three days post-transfection of 10B1-JCV with the new control DNA (hCMV) and the modified JCV#14-1, JCV#14-3 and JCV#14-5. Both, JCV#14-1, JCV#14-3 show a significant suppression (a 4- and 6-fold decrease, respectively) of infectious JCV particles in comparison to the control.

FIG. 12 shows the results of a hemagglutination (HA) assay performed three days post-transfection of 10B1-JCV with the hCMV control DNA (hCMV) and the modified JCV#14-1, JCV#14-3 and JCV#14-5. Both, JCV#14-1 and JCV#14-3 show a significant suppression (a 4- and 6-fold decrease, respectively) of infectious JCV particles in comparison to the control.

Example 8

Reduction of RNA by 2' O-Methyl RNA Capped Antisense DNAs

Figure 13:
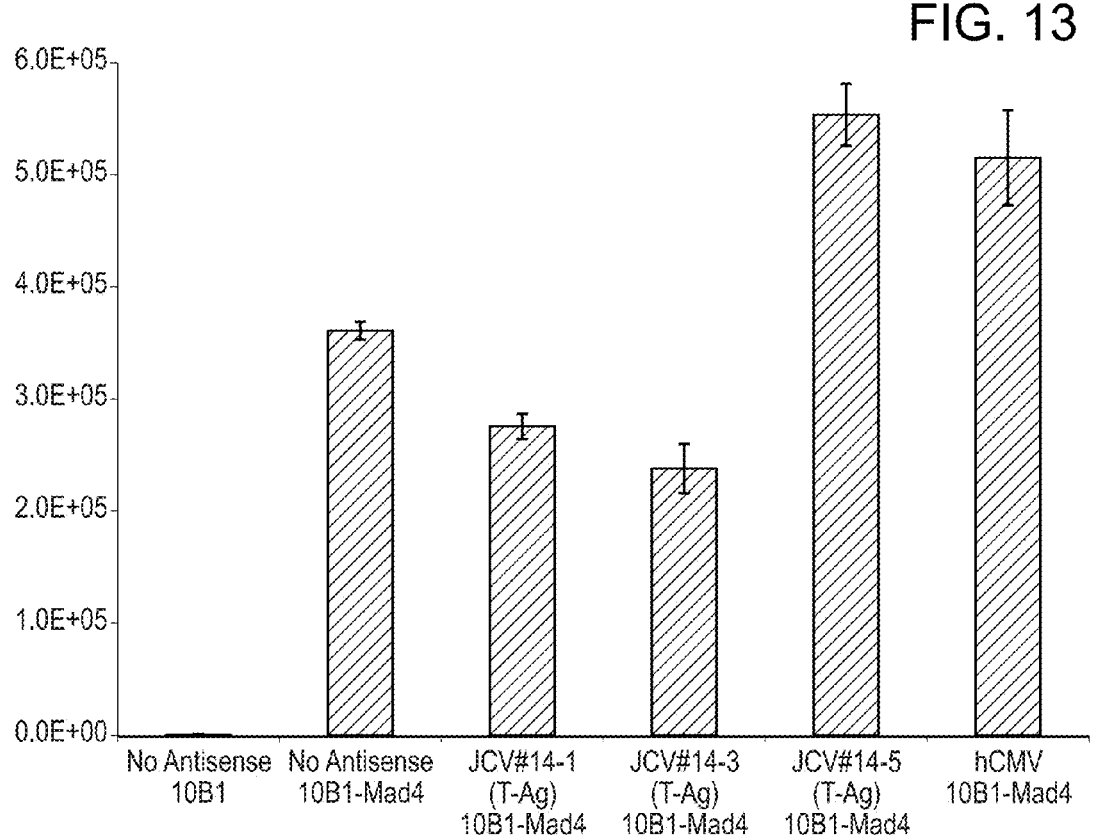
FIG. 13 shows levels of T-Ag RNA in persistently infected 10B1-JCV (10B1-Mad4) cells. Values are expressed as copies of cDNA per ng of reverse transcribed mRNA and were determined by qRT-PCR. Wells were seeded with 100,000 cells, followed by transfection with 0.5 ug antisense DNA. 3 days after transfection, cells were harvested and RNA was isolated. The left-most column is a control of uninfected 10B1 cells. JCV#14-1 and JCV#14-3 transfection caused a reduction in T-Ag RNA as compared to both no antisense and hCMV controls.
Figure 14:
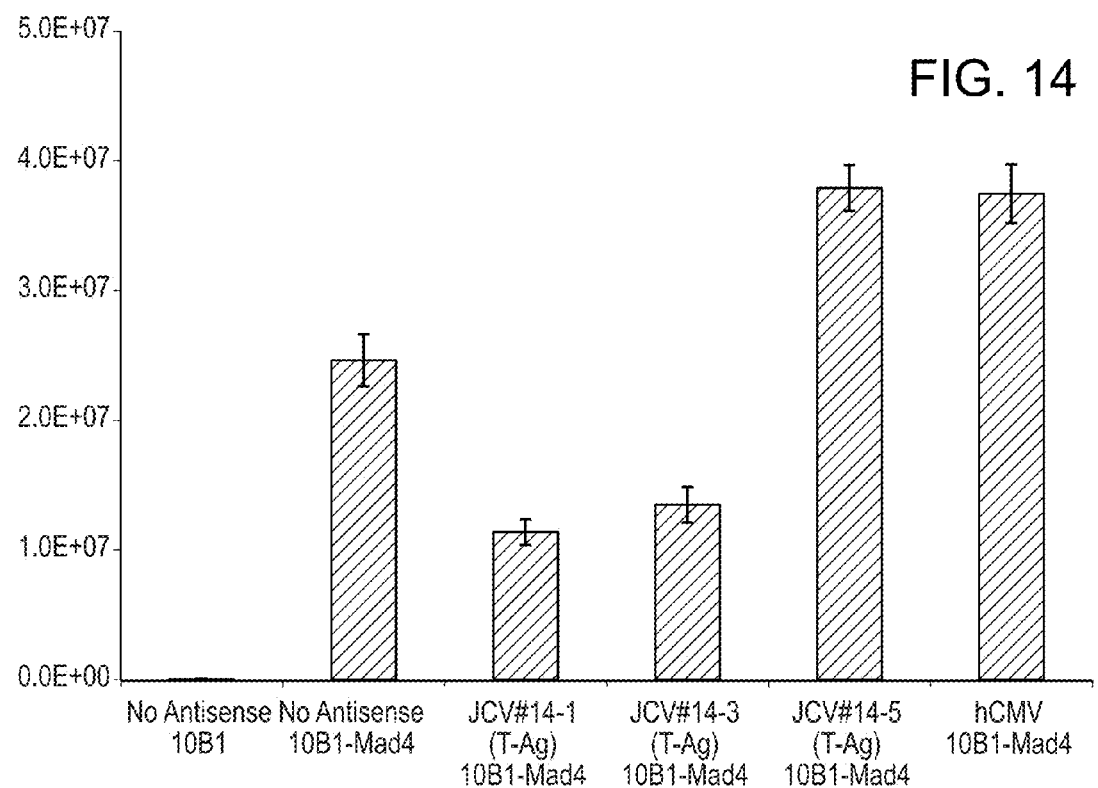
FIG. 14 shows levels of VP1 RNA in persistently infected 10B1-JCV (10B1-Mad4) cells. Values are expressed as copies of cDNA per ng of reverse transcribed mRNA and were determined by qRT-PCR. Wells were seeded with 100,000 cells, followed by transfection with 0.5 ug antisense DNA. 3 days after transfection, cells were harvested and RNA was isolated. The left-most column is a control of uninfected 10B1 cells. JCV#14-1 and JCV#14-3 transfection caused a reduction in VP1 RNA as compared to both no antisense and hCMV controls. This may be due to a reduction in T-Ag protein, which drives VP1 transcription.

In order to examine the direct effects of antisense DNA on T-Ag and VP1 RNA, a set of experiments were performed on persistently infected 10B1-JCV cells (also called 10B1-Mad4). 100,000 cells were seeded per well and transfected with 0.5 ug of antisense DNAs. 3 days post transfection, cells were harvested and RNA was isolated. RNA was reverse transcribed and quantified by qRT-PCR using a standard curve of serial pM1TC dilutions. Uninfected 10B1 cells served as a negative control. T-Ag cDNA was quantified as cDNA copies per ng RNA (FIG. 13). Both JCV#14-1 and JCV#14-3 caused a reduction in JCV T-Ag RNA as compared to both the no antisense control and hCMV antisense control (FIG. 13). Additionally, both JCV#14-1 and JCV#14-3 antisense DNAs caused a reduction in the copy number of VP1 RNA as compared to controls (FIG. 14). This may be due to the necessity of T-Ag protein to drive transcription of VP1.

Example 9

Test of the Monoclonal Antibodies Directed Against JCV#14-1

In this group of experiments, the evaluation of the monoclonal antibodies against the modified JCV #14 (JCV14-1) was assessed. The sequence for JCV#14-1 (/5Phos/mCA*G*G*T*C*T*T*C*A*T*C*C*C*A*C*T*T*C*TmC) (SEQ ID NO: 24) was sent to the company GenScript for the production of monoclonal antibodies. The company produced 20 different antibody clones directed against JCV14-1 antisense DNA (reported in the table below in the "Cell line" columns). OD 450 is the optical density of the supernatant, indicated the amount of antibody present.

| Cell line | OD 450 |
|---|---|
| 1A11 | 2.739 |
| 1B5 | 2.438 |
| 3H4 | 2.304 |
| 4D5 | 2.344 |
| 5D7 | 2.317 |
| 5F11 | 2.748 |
| 7E5 | 2.421 |
| 7F5 | 2.739 |
| 7G3 | 2.337 |
| 11B7 | 2.587 |
| 11C4 | 2.137 |
| 11C5 | 2.124 |
| PC(antiserum 1:1k) | 2.752 |
| 11D12 | 2.571 |
| 11H9 | 2.415 |
| 13C4 | 1.872 |
| 14G2 | 1.920 |
| 15G7 | 2.066 |
| 16A4 | 2.430 |
| 16C3 | 2.277 |
| 16E11 | 2.545 |
| 18G1 | 2.211 |
| 18H9 | 2.076 |
| 19G8 | 1.778 |
| 20C7 | 2.319 |
| NC(medium) | 0.059 |

Figure 15:
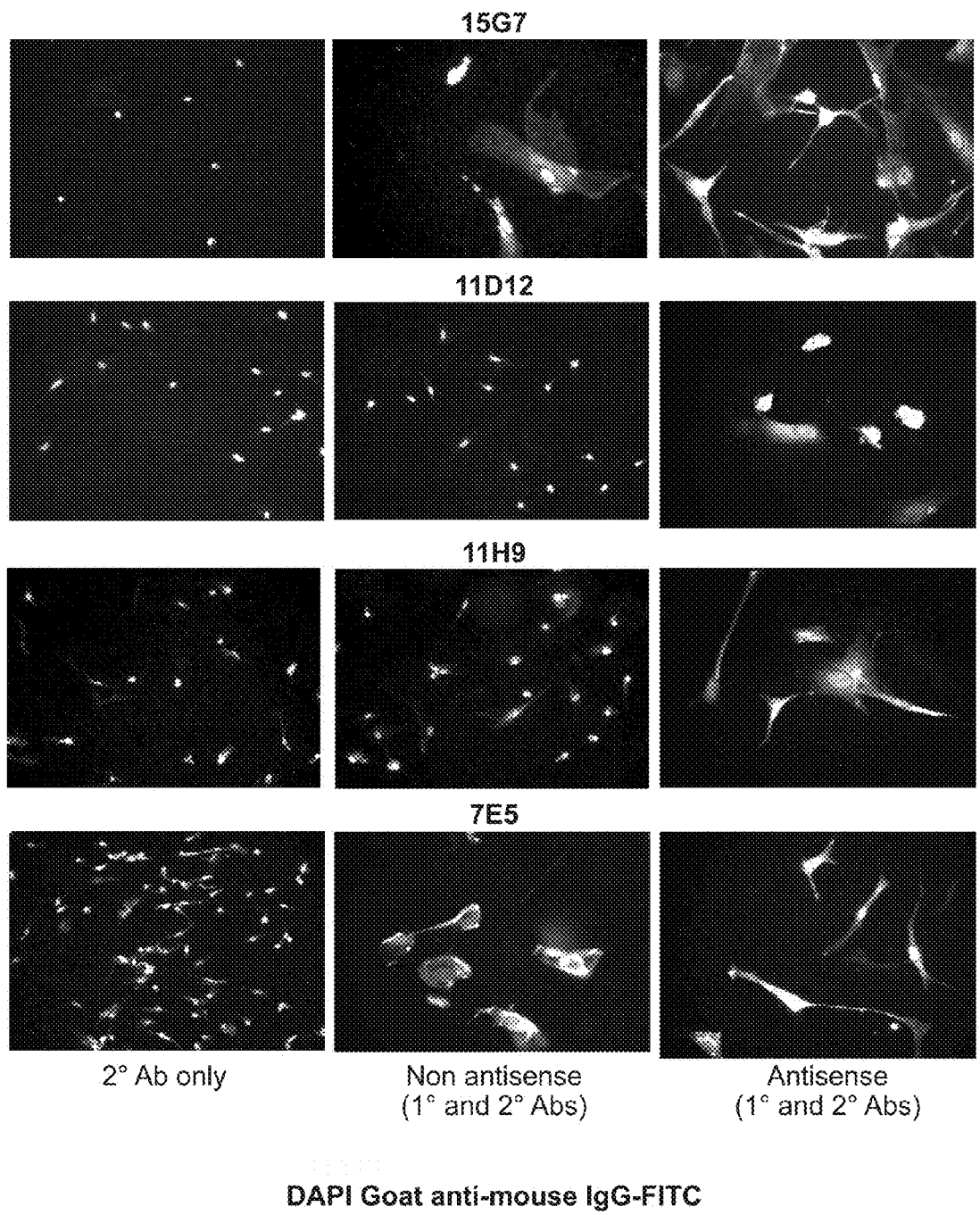
FIG. 15 shows the detection of antisense DNA in transfected cells. Immunofluorescence imagines were obtained from PDA cells transfected with JCV#14-1 and stained using supernatants derived from 20 different monoclonal antibodies directed against the JCV#14-1 antisense oligodeoxynucleotide. The clones were generated by the company GenScript and screened by ELISA. The sensitivity and specificity of the each supernatants were tested on PDA cells transfected with JCV#14-1 antisense. For each experiment two negative controls were performed. One negative control consisted of PDA cells transfected with JCV#14-1 and stained only with the secondary antibody (gam-IgG-FITC) while the other was PDA cells non-transfected with the antisense, but stained with both primary and secondary antibodies. The third condition consisted of PDA cells transfected with JCV#14-1 and stained with both primary and secondary antibodies. Each monoclonal antibody was tested in duplicate. IFA data showed that some of the supernatant have a non-specific staining (data not shown), but we were able to select four (15G7, 7E5, 11D12, 11H9) that provided the best discrimination between cells transfected with the selected antisense from those not transfected.

Those clones were subsequently tested by immunofluorescence (IFA) for their sensitivity and specificity to the antisense JCV#14-1. Each experiment included two independent negative controls. One negative control consisted of PDA cells transfected with JCV#14-1 and stained only with the secondary antibody (gam-IgG-FITC) while the other was PDA cells non transfected with the antisense, but stained with both primary and secondary antibodies. The third condition consisted of PDA cells transfected with JCV#14-1 and stained with both primary and secondary antibodies. Each monoclonal antibody was tested in duplicate. IFA data showed that four monoclonals (15G7, 7E5, 11D12, 11H9) provided the best discrimination between cells transfected with the selected antisense and those not transfected (FIG. 15). The other 16 supernatants were not specific for the antisense DNA and showed non-specific staining (data not shown), Example 10

On-Going and Planned Studies

Studies will measure the distribution of antisense molecules after implantation in mouse brain tissue using fluorescent labeled nucleotides. Further toxicology studies are planned in non-human primates and/or rodents for the candidate antisense nucleotides to determine tissue distribution in multiple organs and any occurrence of pathology resulting from the presence of the antisense molecules.
Methods
The foregoing Examples were carried out with, but not limited to, the following methods and materials.
Virus, Plasmid and Cells.

JCV is a polyomavirus responsible for Progressive Multifocal Leukoencephalopathy (PML), a demyelinating disease of the central nervous that results from the lytic infection of oligodendrocytes by the virus. JCV replicates in limited cell types in culture, predominantly in human glial cells. Progenitor-derived astrocytes (PDA), originated from human fetal neural progenitor cells, have been used in this study because susceptible to JCV infection. PDA cells were maintained in minimal essential medium (MEM, Cellgro) supplemented with 10% FBS, 2 mM L-glutamine and 50 ug/ml gentamicin. 10B1 cells were subcloned from SVG cell line. SVG cells were previously generated by transfecting human fetal brain cultures with an origin-defective SV40 mutant. The resultant culture of multiple phenotypes of neural derived cells became immortalized by stable expression of SV40 T antigen (Major et al., 1985; U.S. Pat. No. 4,707,448).

10B1 subset of SVG was highly permissive for JCV DNA replication and gene expression and supported persistent and stable JCV infection over months in culture (Ferenczy et al. 2013). Persistently JCV-infected 10B1 cells were also used in this study. 10B1-JCV cells-43-were generated from positive cloning of Mad 4 JCV-infected SVG cells (Major et al., 1985), which showed stable expression of JCV T antigen (T-Ag). Both 10B1 and 10B1-JCV were maintained in MEM containing 10% FBS, 2 mM L-glutamine and 50 ug/ml gentamicin.

JCV isolates of Mad-1 and Mad-4 were originally derived from PML patients (Frisque, 1983). The Mad-4 isolate of JCV was chosen in this study because it is considered representative of other isolates obtained from the brains of PML patients. The Mad-4 isolate of JCV was grown in and purified from PDA (Messam et al., 2003). Virus titer was determined by hemagglutination of human type 0 erythrocytes and is expressed as hemagglutinin units (HAU) (Major et al, 1985). One HAU of Mad-4 virus contains $1 \times 10^4$ infectious particles.

The plasmid of pM1TC was constructed by ligation of the full genome of JCV Mad-1 into plasmid vector pBR322 (Frisque, 1983). The plasmid was transformed into competent bacteria and cloned in selective media. After expansion of positive colony, DNA was extracted for both validation with restriction enzyme digestion and sequencing, and cell transfection.
JC Virus Infection.

PDA cells were seeded at densities of $1.5 \times 10^5$ to $2.5 \times 10^5$ cells per well in 6-well plates. In one embodiment, PDA cells were seeded at densities of $0.5 \times 10^4$ cells per well in 6-well plates. Cells were grown 2 days at 37° C. The culture medium was then removed, and cells were washed 3 times with phosphate-buffered saline (PBS). Cells were exposed to a minimal volume of PBS containing Mad-4 JCV at a concentration of 200 HAU per 1×10⁶ cells for 90 min Culture medium was added to each well to the nominal volume of the culture plate. The non-infected control cultures were incubated with PBS for 90 min in the absence of virus. After overnight exposure to JCV, the cultures medium was replaced with the medium containing no antibiotics to create a favorite environment for transfection with antisense DNA.

Antisense DNAs and Transfection/Co-Transfection.

The antisense DNAs were designed to target products of different coding regions of JCV (FIG. 1).

Lg-T1 (5'-G*A*A*T*C*C*A*T*G* G*A*G*C*T*T* A*T*G*G*A-3') (SEQ ID NO: 16) and Lg-T2 (5'-A*G*A*A*C*T*C*C* A*C*C*C* T*G* A*T*A*A*A*G-3') (SEQ ID NO: 17) target small t, large T and T splice variants; JCV#3 (5'-G*T*C*T*T*C*A*T*C*C* C* A*C*T*T* C*T*C*A*T-3') (SEQ ID NO: 11) and JCV#14 (5'-C*A*G*G*T* C*T*T*C*A*T*C*C*C*A* C*T*T*C*T*C-3') (SEQ ID NO: 14) target large T and small t; JCV#8 (5'-C*T*C*C*A*C*A*A*T*C*T*C*C*C*A*G*G*C*T*T-3') (SEQ ID NO: 5) and JCV#13 (5'-G*T*T*C*T*C* C*A*C*A*A*T*C*T*C*C*C*A*G* G-3') (SEQ ID NO: 10) target VP2/VP3; VP1-2 (5'-T*T*G*G*A*A*C*T* T*G*C*A* C*G*G-3') (SEQ ID NO: 19), VP1-3 (5'-T*T*C*T*A*C*C*T*C*T*G*T*A*A*T*T*G*A*G*T* C-3') (SEQ ID NO: 20) and VP1-4 (5'-T*T*G*T*C*A*A*C*G*T*A*T*C*T*C*A*T*C*A*T*G-3') (SEQ ID NO: 21) target VP1. In addition, two mismatched (or randomly distributed) antisense oligonucleotides are also synthesized as experimental control and assigned the names as scramble 1 (5'-G*A*T*C*T*G* A*G*T*T*C*A*G*A*G* T*T*C*C*A*G-3') (SEQ ID NO: 22) and scramble 3 (22-mer, 5'-C*A*G*T*G*T* G*T*G*T*C*T*G*A*G*A* A*G*C*T*C*A-3') (SEQ ID NO: 23).

2' O-methyl RNA bases were added to the 5' and 3' ends of JCV#14 in Examples 7 and 8 JCV#14-1 (mC*A*G*G*T*C*T*T*C*A*T*C*C*C*A*C*T*T*C*TmC) (SEQ ID NO: 25), JCV#14-3 (mC*mA*mG*G*T*C*T*T*C*A*T*C*C*C*A*C*T*mU*mC*TmC) (SEQ ID NO: 26), JCV#14-5 (mC*mA*mG*mG*mU*C*T*T*C*A*T*C*C*C*A*mC*mU*mC*TmC) (SEQ ID NO: 27). The oligonucleotides were synthesized by phosphorothioate chemistry at Integrated DNA Technologies.

PDA cells (JCV infection model) or 10B1-JCV cells, at 70-90% confluence, were transfected with different concentrations of antisense DNA (see Results) using Lipofectamine™ 2000 Transfection Reagent (Invitrogen) according to the manufacturer's instructions. The cultures were rinsed with plan medium to remove transfection complex 4 hours later, and then maintained in the normal culture medium for 15 and 2 days, respectively. In pM1TC model, the PDA cells at 70-90% confluence were co-transfected for 4 hours with 4.5 ug/well pM1TC and different concentrations of antisense DNA (see Results) using the same reagent as above. The cells were then maintained at 37° C., 5% CO₂ for 5 days.

Quantitative Immunofluorescence.

Immunofluorescence labeling was conducted on Lipofectamine 2000-transfected cell cultures. Cells were fixed and permeabilized with 1:1 (v/v) methanol/acetone before indirect antibody labeling. Following a blockage with Hanks buffer containing 2% normal horse serum, 10% normal goat serum and 1 mM HEPES (HHG), the samples were incubated at RT with 1:100 mouse IgG$_{2a}$ anti-(SV40)T-Ag (DP02, Calbiochem) in HHG or 1:500 mouse IgG1 anti-JCV VP1 (NCL-JC-BK, Novo Castra) in HHG for 1 h. After 3 times' rinse with PBS, the samples were incubated at RT with 1:500 goat anti-mouse IgG with AF488-conjugation (A21131, FITO) or 1:1000 goat anti-mouse IgG1 with FITC-conjugation (Invitrogen) and 1:500 DAPI (D1306, Molecular Probes) in HHG. Samples were finally mounted with a glycerol-based mounting medium and analyzed by fluorescence microscopy using a Zeiss Axiovert 200M microscope fitted with filters appropriate for DAPI and Alexa-Fluor-488 excitation.

In Situ Hybridization.

Replication of viral DNA in JCV-infected PDA cells or 10B1-JCV cells was detected by in situ DNA hybridization using a JCV biotinylated-DNA BioProbe over the full genome (Enzo Life Sciences, Inc., New York, N.Y.) as previously described (Houff et al., 1989). Calf thymus DNA was used as a nonspecific control for the JCV probe. A brown precipitate in the nuclei of cells is indicative of a positive signal for JCV DNA. The samples were counterstained with hematoxilyn. The total number of JCV-positive cells was counted per sample from the 18-mm by 18-mm coverslip.

Microscopy and Image Analysis.

Immunofluorescence labeled or hybrid-positive cells were count over coverslip under 200× using a fluorescent or a bright-field microscope, respectively. To determine the total cell number per coverslip, images were acquired at 5 random positions at ×100 magnification. Cells were counted throughout each image using ImageJ (Rasband, 2012), and the average cell number per photo was converted to cell number per coverslip at final stage. The final data was generated by normalization of positive cell number against total cell number.

Statistics.

The data are expressed as mean percentages of the JCV-infected, non-treated-control value±standard deviations (SD). In experiments testing non-infected cells, data are expressed as mean percentages of the non-treated control value±SD. Data were statistically evaluated at a significance level of 1% with one- or two-way analysis of variance (ANOVA) by using the software VassarStats followed by the Tukey honestly significant difference (HSD) test.

Antisense DNAs Transfection.

10B1 and 10B1-JCV cell lines were plated at 5e4 cells/well in triplicates. The day after, cells were with antisense DNA at 0.5 μg/5⁴ cells using Lipofectamine 2000 (Life Technologies). The manufacturer's instructions were modified to best adapt them to our cell culture conditions. Briefly, the cells were rinsed with OPTI-MEM (Gibco) medium, and then the transfection complex was added with a ratio of DNA to lipofectamine of 1:20. Cells and transfection complex were incubated for 4 hrs. at 37° C. in 5% CO2. After this incubation, the transfection complex was gently removed and the cells were rinse once in medium without serum. Then 2 ml of medium completed with serum was added to the cultures and the cells were incubated for 3 days at 37° C. before harvest them for the experiments. It is noted that the transfection protocol used in the experiments described herein differs considerably from the standard protocol supplied by the manufacturer for Lipofectamine in concentration and kinetics of application. The protocol described herein for transfection was independently determined and optimized by experimentation.

Hemagglutination Assay (HA).

The hemagglutination assay is a method of quantification for viruses by hemagglutination of red blood cells. One hemagglutination unit (HAu) contains approximately 1×10⁴ infectious particles. Hemagglutination titers are expressed as the reciprocal of the final dilution resulting in hemagglutination of human type-0 erythrocytes.

Isolation of Nucleic Acids

Total RNA was isolated as in Ferenczy, et al, 2013 using Trizol reagent (Ambion), extracted with chloroform, then purified using the RNeasy plus mini kit (Qiagen) according to the manufacturer's instructions, with an on-column DNase step, and was eluted from the column in nuclease-free water and quantified on a Nanodrop 8000 (Thermo Scientific). Total DNA was isolated as in (Ferenczy, et al, 2013) by cell lysis with SDS lysis buffer, followed by proteinase K treatment, phenol chloroform extraction, and ethanol precipitation. DNA was resuspended in nuclease-free water and quantified on a Nanodrop 8000 (Thermo Quantitative Reverse Transcription Real Time PCR (qRT-PCR)

Equal amounts of RNA were reverse transcribed with Taqman reverse transcription reagents (Life Technologies) using oligo(dT) primers according to the manufacturer's instructions. JCV T antigen mRNA present in infected cells was measured using the TaqMan one-step RT-PCR master mix reagents (Applied Biosystems) and the primer/probes described for JCV genome quantification. mRNA values were adjusted based on values from no-RT control reactions. JCV VP-1 mRNA present in infected cells was measured using the Power SYBR Green RNA-to-CT kit (Applied Biosystems) with the forward (JLP15 5'-ACAGTGTGGC-CAGAATTCCACTACC-3') (SEQ ID NO: 28) and the reverse (JLP16 5'-TAAAGCCTCCCCCCCAACAGAAA-3') (SEQ ID NO: 29) primers previously described (Agostini et al. 1997) according to manufacturer's instructions. Eight ten-fold serial dilutions of Mad-1 plasmid (pM1TC) were prepared to generate a standard curve to determine JCV copy number. mRNA values were adjusted based on values from no-RT control reactions.

Quantitative PCR (qPCR) for JC Virus Genome Quantification

JCV DNA present in infected cells was measured by detecting a unique and conserved short region in the JCV T antigen gene using the TaqMan gene expression master mix reagents (Applied Biosystems), the forward primer JCT1 (5'-AGAGTGTTGGGATCCTGTGTTTT-3') (SEQ ID NO: 30), reverse primer JCT2 (5'-GAGAAGTGGGGAT-GAAGACCTGTTT-3') (SEQ ID NO: 31), and FAM/TAMRA labeled probe JCT1.1 (5'-6FAMTCATCACTG-GCAAACATTTCTTCATGGCTAMRA-3') (SEQ ID NO: 32) according to the manufacturer's instructions. Eight ten-fold serial dilutions of Mad-1 plasmid (pM1TC) were prepared to generate a standard curve to determine JCV genome copy number. Copy number was normalized to total DNA concentration.

Equivalents

Those skilled in the art will recognize, or be able to ascertain using no more than routine experimentation, many equivalents to the specific embodiments of the invention described herein. Such equivalents are intended to be encompassed by the following claims.

Incorporation by Reference

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference.

REFERENCES

Altschul S F, Gish W, Miller W, Myers E W, Lipman D J. 1990. Basic local alignment search tool. J Mol Biol. October 5; 215(3):403-10.

Bollag B, Hofstetter C A, Reviriego-Mendoza M M, Frisque R J. 2010. J C virus small T antigen binds phosphatase PP2A and Rb family proteins and is required for efficient viral DNA replication activity. PLoS One 5:e10606.

Cinque P, Koralnik I J, Gerevini S, Miro J M, Price R W. 2009. Progressive multifocal leukoencephalopathy in HIV-1 infection. Lancet Infect. Dis. 9:625-36.

Clifford D B, Nath A, Cinque P, Brew B J, Zivadinov R, Gorelik L, Zhao Z, Duda P. 2013. A study of mefloquine treatment for progressive multifocal leukoencephalopathy: results and exploration of predictors of PML outcomes. J Neurovirol. 2013 August; 19(4):351-8.

Cole C N. 1996. Polyomavirinae: the viruses and their replication, p 917-946. In Fields B N, De Mesmaeker A, Haner R, Moser H E. 1995. Antisense oligonucleotides. Acc. Chem. Res., 28, 366-374.

Dias N, Stein C A. 2002. Antisense oligonucleotides: basic concepts and mechanisms. Mol. Cancer Ther. 1:347-355.

Dugan A S, Gasparovic M L, Atwood W J. 2008. Direct correlation between sialic acid binding and infection of cells by two human polyomaviruses (J C virus and B K virus). J. Virol. 82:2560-2564.

Egli A, Infanti L, Dumoulin A, Buser A, Samaridis J, Stebler C, Gosert R, Hirsch H H. 2009. Prevalence of polyomavirus B K and J C infection and replication in 400 healthy blood donors. J. Infect. Dis. 199:837-846.

Elphick G F, Querbes W, Jordan J A, Gee G V, Eash S, Manley K, Dugan A, Stanifer M, Bhatnagar A, Kroeze W K, Roth B L, Atwood W J. 2004. The human polyomavirus, JCV, uses serotonin receptors to infect cells. Science 306:1380-1383.

Ferenczy M W, Marshall I I, Nelson C D. S, Atwood W J, Nath A, Khalili K, Major E O. 2012. Molecular biology, epidemiology, and pathogenesis of progressive multifocal leukoencephalopathy, the J C virus-induced demyelinating disease of the human brain. Clin. Microbiol. Rev. 25:471-506.

Ferenczy M W, Johnson K R, Steinberg S M, Marshall U, Monaco M C, Beschloss A M, Jensen P N, Major E O. 2013 Clonal immortalized human glial cell lines support varying levels of J C virus infection due to differences in cellular gene expression. J Neuroimmune Pharmacol. 2013 December; 8(5):1303-19.

Frisque R J. 1983. Regulatory sequences and virus-cell interactions of J C virus. Prog. Clin. Biol. Res. 105:41-59.

Frisque R J, Bream G L, Cannella M T. 1984. Human polyomavirus J C virus genome. J Virol. 1984 August; 51(2):458-69.

Houff S A, Katz D, Kufta C V, Major E O. 1989. A rapid method for in situ hybridization for viral DNA in brain biopsies from patients with AIDS. AIDS 3:843-845.

Jensen P N, Major E O. 1999. Viral variant nucleotide sequences help expose leukocytic positioning in the J C virus pathway to the CNS. J. Leukoc. Biol. 65:428-438

Johnson E M. 2010. Structural evaluation of new human polyomaviruses provides clues to pathobiology. Trends Microbiol. 18:215-223.

Johnson E M, Chen P L, Krachmarov C P, Barr S M, Kanovsky M, Ma Z W, Lee W H. 1995. Association of human Pur alpha with the retinoblastoma protein, Rb, regulates binding to the single-stranded DNA Pur alpha recognition element. J. Biol. Chem. 270:24352-24360.

Jones R, Kunsman G, Levine B, Smith M, Stahl C. 1994. Mefloquine distribution in postmortem cases. Forensic. Sci. Int. 68:29-32.

Kean J M, Rao S, Wang M, Garcea R L. 2009. Seroepidemiology of human polyomaviruses. PLoS Pathog. 5:e1000363

Knipe D M, Howley P M (ed), Fundamental virology, 3rd ed, Lippincott, Williams & Wilkins, Philadelphia.

Lynch K J, Frisque R J. 1990. Identification of critical elements within the J C virus DNA replication origin. J. Virol. 64:5812-5822.

Lynch K J, Haggerty S, Frisque R J. 1994. DNA replication of chimeric J C virus-simian virus 40 genomes. Virology 204:819-822.

Ma Y, Wang N, Li M, Gao S, Wang L, Zheng B, Qi Y, Ruan Q. 2012. Human CMV transcripts: an overview. Future Microbiol. May; 7(5):577-93.

Marshall U, Major E O. 2010. Molecular regulation of J C virus tropism: insights into potential therapeutic targets for progressive multifocal leukoencephalopathy. J. Neuroimmune Pharmacol. 5:404-417.

Mateen F. J, Muralidharan R, Carone M, Van De Beek D, Harrison D M, Aksamit A J, Gould M S, Clifford D B, Nath A. 2011. Progressive multifocal leukoencephalopathy in transplant recipients. Ann. Neurol. 70:305-322.

Major E O, Miller A E, Mourrain P, Traub R G, de Widt E, Sever J. 1985. Establishment of a line of human fetal glial cells that supports J C virus multiplication. Proc. Natl. Acad. Sci. U.S.A. 82:1257-1261.

Major E O. 2010. Progressive multifocal leukoencephalopathy in patients on immunomodulatory therapies. Annu Rev Med. 2010; 61:35-47.

Merabova N, Kaniowska D, Kaminski R, Deshmane S L, White M K, Amini S, Darbinyan A, Khalili K. 2008. J C virus agnoprotein inhibits in vitro differentiation of oligodendrocytes and promotes apoptosis. J. Virol. 82:1558-1569.

Messam C A, Hou J, Gronostajski R M, Major E O. 2003. Lineage pathway of human brain progenitor cells identified by J C virus susceptibility. Ann Neurol. 53:636-646.

Neu U, Maginnis M S, Palma A S, Stroh L J, Nelson C D, Feizi T, Atwood W J, Stehle T. 2010. Structure-function analysis of the human J C polyomavirus establishes the LSTc pentasaccharide as a functional receptor motif. Cell Host Microbe 8:309-319.

Nukuzuma S, Nakamichi K, Nukuzuma C, Takegami T. 2009 Inhibitory effect of serotonin antagonists on J C virus propagation in a carrier culture of human neuroblastoma cells. Microbiol. Immunol. 53:496-501.

O'Hara B A, Atwood W J. 2008. Interferon beta1-a and selective anti-5HT(2a) receptor antagonists inhibit infection of human glial cells by J C virus. Virus Res. 132:97-103.

Okada Y, Endo S, Takahashi H, Sawa H, Umemura T, Nagashima K. 2001. Distribution and function of JCV agnoprotein. J. Neurovirol. 7:302-306.

Orba Y, Sawa H, Iwata H, Tanaka S, Nagashima K. 2004 Inhibition of virus production in J C virus-infected cells by postinfection RNA interference. J. Virol. 78:7270-7273.

Ou W C, Chen L H, Wang M, Hseu T H, Chang D. 2001. Analysis of minimal sequences on J C virus VP1 required for capsid assembly. J. Neurovirol. 7:298-301.

Pham Y T, Nosten F, Farinotti R, White N J, Gimenez F. 1999. Cerebral uptake of mefloquine enantiomers in fatal cerebral malaria. Int. J. Clin. Pharmacol. Ther. 37:58-61.

Portnoy V, Huang V, Place R F, Li L C. 2011. Small RNA and transcriptional upregulation. Wiley Interdiscip. Rev. RNA 2:748-760.

Pruitt A A. 2012. CNS infections in patients with cancer. Continuum (Minneap Minn) 18:384-405.

Radhakrishnan S, Gordon J, Del Valle L, Cui J, Khalili K. 2004. Intracellular approach for blocking J C virus gene expression by using RNA interference during viral infection. J. Virol. 78:7264-7269.

Radulescu R T. 1995. The 'LXCXE' hydropathic superfamily of ligands for retinoblastoma protein: a proposal. Med. Hypotheses. 44:28-31.

Rakoczy P E. 2001. Antisense DNA technology. Methods Mol. Med. 47:89-104.

Rasband W S. 2012. ImageJ, U. S. National Institutes of Health, Bethesda, Md., USA, http://imagej.nih.gov/ij/.

Sadiq S A, Puccio L M, Brydon E W. 2010. JCV detection in multiple sclerosis patients treated with natalizumab. J. Neurol. 257:954-958.

Saribas A S, White M K, Safak M. 2012. J C virus agnoprotein enhances large T antigen binding to the origin of viral DNA replication: evidence for its involvement in viral DNA replication. Virology 433:12-26.

Schaumburg C, O'Hara B A, Lane T E, Atwood W J. 2008. Human embryonic stem cell-derived oligodendrocyte progenitor cells express the serotonin receptor and are susceptible to J C virus infection. J. Virol. 82:8896-8899.

Shishido-Hara Y, Ichinose S, Higuchi K, Hara Y, Yasui K. 2004. Major and minor capsid proteins of human polyomavirus J C cooperatively accumulate to nuclear domain 10 for assembly into virions. J. Virol. 78:9890-9903.

Suzuki T, Orba Y, Okada Y, Sunden Y, Kimura T, Tanaka S, Nagashima K, Hall W W, Sawa H. 2010. The human polyoma J C virus agnoprotein acts as a viroporin. PLoS Pathog. 6:e1000801.

Suzuki T, Semba S, Sunden Y, Orba Y, Kobayashi S, Nagashima K, Kimura T, Hasegawa H, Sawa H. 2012. Role of J C virus agnoprotein in virion formation. Microbiol. Immunol. 56:639-646.

Tan K, Roda R, Ostrow L, McArthur J, Nath A. 2009. PML-IRIS in patients with HIV infection: clinical manifestations and treatment with steroids. Neurology 72:1458-1464.

Toovey S. 2009. Mefloquine neurotoxicity: a literature review. Travel Med. Infect. Dis. 7:2-6.

Wang M, Tsou T H, Chen L S, Ou W C, Chen P L, Chang C F, Fung C Y, Chang D. 2004. Inhibition of simian virus 40 large tumor antigen expression in human fetal glial cells by an antisense oligodeoxynucleotide delivered by the J C virus-like particle. Hum. Gene Ther. 15:1077-1090.

Weinberg R A. 1995. The retinoblastoma protein and cell cycle control. Cell 81:323-330.

Weinberg R A. 1996. E2F and cell proliferation: a world turned upside down. Cell 85:457-459.

White M K, Johnson E M, Khalili K. 2009. Multiple roles for Puralpha in cellular and viral regulation. Cell Cycle 8:1-7.

Whitehead K A, Dahlman J E, Langer R S, Anderson D G. 2011. Silencing or stimulation? siRNA delivery and the immune system. Annu. Rev. Chem. Biomol. Eng. 2:77-96.

Zhang J, Madden T L. 1997. PowerBLAST: a new network BLAST application for interactive or automated sequence analysis and annotation. Genome Res. 1997 June; 7(6): 649-56.

What is claimed is:

1. An antisense oligonucleotide comprising:
   a nucleic acid sequence at least 90% identical to a nucleic acid sequence selected from the group consisting of: SEQ NO: 11, 12, 13, 14, 15, 16, 17, 19, and 20
   at least one non-naturally occurring modification,
   wherein the oligonucleotide is targeted to a nucleic acid encoding polyomavirus JC (JCV), and is capable of inhibiting JCV replication and multiplication.

2. The antisense oligonucleotide of claim 1, wherein the non-naturally occurring modification includes at least one phosphorothioate backbone modification.

3. The antisense oligonucleotide of claim 1, wherein the oligonucleotide has a phosphorothioate backbone.

4. The oligonucleotide of claim 2, wherein the non-naturally occurring modification further includes at least one methylribose backbone modification.

5. The antisense oligonucleotide of claim 1, wherein the non-naturally occurring modification includes at least one methylribose backbone modification.

6. The oligonucleotide of claim 1, further comprising at least one 2' sugar modification.

7. The antisense oligonucleotide of claim 5, wherein the oligonucleotide has a phosphorothioate backbone.

8. The antisense oligonucleotide of claim 2, further comprising at least one 2' sugar modification.

9. The antisense oligonucleotide of claim 1, wherein the nucleic acid sequence is at least 99% identical to a nucleic acid sequence selected from the group consisting of: SEQ NO: 11, 12, 13, 14, 15, 16, 17, 19, and 20.

10. The antisense oligonucleotide of claim 1, wherein the nucleic acid sequence is at least 95% identical to a nucleic acid sequence selected from the group consisting of: SEQ NO: 11, 12, 13, 14, 15, 16, 17, 19, and 20.

11. The antisense oligonucleotide of claim 1, wherein the nucleic acid sequence consists of a nucleic acid sequence selected from the group consisting of: SEQ ID NO: 11, 12, 13, 14, 15, 16, 17, 19, and 20.

12. A pharmaceutical composition comprising one or more oligonucleotides of claim 1, and a pharmaceutical carrier.

13. A method of inhibiting JCV replication or multiplication in a subject, comprising administering to the subject the pharmaceutical composition of claim 12.

14. A method of treating a subject having or at risk for having progressive multifocal leukoencephalopathy (PML), comprising administering to the subject an effective amount of the pharmaceutical composition of claim 12, thereby treating PML.

15. A method of reducing the risk of developing PML in a subject infected with JCV comprising administering to the subject an effective amount of the pharmaceutical composition of claim 12.

16. The method of claim 13, wherein the subject is an immunosuppressed or immunocompromised subject.

17. The method of claim 13, further comprising administration of an additional agent.

18. A kit comprising one or more oligonucleotides of claim 1.

19. The kit of claim 18, further comprising instructions for use for inhibiting JCV replication or multiplication.

* * * * *